United States Patent [19]
Cerri et al.

[11] Patent Number: 5,705,531
[45] Date of Patent: Jan. 6, 1998

[54] 1,5-DISUBSTITUTED 7A-METHYLPERHYDROINDEN-3A-OL DERIVATIVES, USEFUL IN TREATING CARDIOVASCULAR DISORDERS, PROCESSES FOR THEIR PREPARATION AND PHARMACEUTICAL COMPOSITIONS CONTAINING THE SAME

[75] Inventors: Alberto Cerri, Gessate; Nicoletta Almirante; Giuseppe Bianchi, both of Milan; Patrizia Ferrari, Varese; Piero Melloni, Bresso, all of Italy

[73] Assignee: Sigma-Tau Industrie Farmaceutiche Riunite S.p.A., Rome, Italy

[21] Appl. No.: 556,854

[22] Filed: Nov. 2, 1995

[30] Foreign Application Priority Data

Nov. 7, 1994 [IT] Italy ................. RM94A0715

[51] Int. Cl.$^6$ .............. A61K 31/155; C07C 279/02
[52] U.S. Cl. .............. 514/634; 514/633; 514/641; 514/659; 564/225; 564/227; 564/229; 564/230; 564/253; 564/254
[58] Field of Search .............. 564/225, 230, 564/227, 229, 253, 254; 514/641, 659, 634, 633

[56] References Cited

U.S. PATENT DOCUMENTS 5,324,719  6/1994  Frigerio et al.
5,444,055  8/1995  Cerri et al.

Primary Examiner—Yogendra N. Gupta
Attorney, Agent, or Firm—Oblon, Spivak, McClelland, Maier & Neustadt, P.C.

[57] ABSTRACT

1,5-Disubstituted 5a-methylperhydroinden-3a-ol derivatives of formula (I):

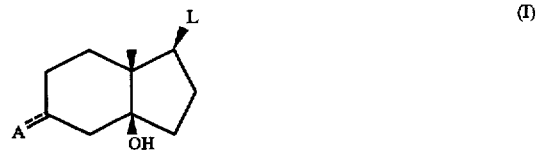

where
either
the symbol - - - - represents a single bond,
the group A is in cis configuration with respect to the 3a-hydroxy, 7a-methyl and 1-L groups, and
A is $(CH=CH)_m$-$(CH_2)_n OR$, $(CH=CH)_m$-$(CH_2)_n NR^1R^2$, $(CH=CH)_m$-$(CH_2)_p B$, OH, $O(CH_2)_q OR$, $O(CH_2)_q NR^1R^2$ or $O(CH_2)_r B$;
q is an integer from 2 to 5;
r is an integer from 1 to 2;
or
the symbol - - - - represents a double bond,
A is oxygen, $CH$-$(CH=CH)_s$-$(CH_2)_n OR$, $CH$-$(CH=CH)_s$-$(CH_2)_n NR^1R^2$ or $CH$-$(CH=CH)_s$-$(CH_2)_p B$; and
L is $[CH=C(R^3)]_s CH=NR^4$ or $[CH=C(R^3)]_s CH_2 NHR^4$, in the E configuration, are useful for treating cardiovascular disorders such as heart failure and hypertension.

8 Claims, No Drawings

1,5-DISUBSTITUTED 7A-METHYLPERHYDROINDEN-3A-OL DERIVATIVES, USEFUL IN TREATING CARDIOVASCULAR DISORDERS, PROCESSES FOR THEIR PREPARATION AND PHARMACEUTICAL COMPOSITIONS CONTAINING THE SAME

The present invention relates to new 1,5-disubstituted 7a-methylperhydroinden-3a-ol derivatives, active on the cardiovascular system, to processes for their preparation and to pharmaceutical compositions containing same for the treatment of cardiovascular disorders, such as heart failure and hypertension.

Known 1,5-disubstituted 7a-methylperhydroinden-3a-ol derivatives, like prieurianin (Nakatani M. et al., *Heterocycles*, 1984, 22 (10), 2335; Lidert Z., *J. Nat. Prod.*, 1985, 48(5), 843), hispidins (Pettit G. R. et al., *J. Nat. Prod.*, 1983, 46(3), 379) and rohitukin derivatives (Lidert Z., *J. Nat. Prod.*, 1985, 48(5), 843), are natural products, extracted from plants, with a perhydroindene skeleton, but different from the one concerning this invention as they present a trans junction and are substituted in position 1 with a 3-furyl and in position 5 with a five-, six- or seven membered lacton ring; moreover they present additional different groups in the other positions of the perhydroindene skeleton. Said compounds are reported to have in vitro antileukemic activity, not translated into in vivo antineoplastic effect, or insect antifeedant activity. None of these compounds is reported to have activity on the cardiovascular system. Also (1S,3aS,4S,7aR)-1-(2H-2-oxopyran-5-yl)-3a-hydroxy-4-[2-(5-hydroxy-2-methylphenyl)ethyl]-7a-methylperhydro-inden-5-one is known (Goerlich B., *Planta Med.*, 1973, 23 (1), 39). It shows a perhydroindene skeleton with cis junction but is substituted in position 1, with a lactone ring, and in position 4 with another substituent; no pharmacological activities are reported for this compound.

Surprisingly the compounds of the present invention show good affinity for the $Na^+,K^+$-ATPase receptor and activity on the cardiovascular system.

The compounds of the present invention have general formula (I)

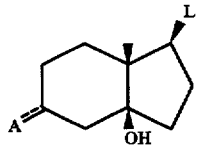

(I)

wherein:

the symbol -------- represents a single or a double bond;

when the symbol -------- represents a single bond the group A is in cis configuration with respect of 3a-hydroxy, 7a-methyl and 1-L groups and A means $(CH=CH)_m$ ⁓$(CH_2)_n OR$, $(CH=CH)_m$ ⁓$(CH_2)_n NR^1 R^2$, $(CH=CH)_m$ ⁓$(CH_2)_p B$, OH, $O(CH_2)_q OR$, $O(CH_2)_q NR^1 R^2$, $O(CH_2)_r B$;

wherein m represents an integer from 0 to 2;
n represents an integer from 1 to 6;
p represents an integer from 0 to 2;
q represents an integer from 2 to 5;
r represents an integer from 1 to 2;
provided that in the same substituent m+n is not greater than 6;

the symbol ⁓ means a Z or E configuration;

R represents hydrogen, $C_1-C_4$ alkyl unsubstituted or substituted by $NR^1 R^2$;

$R^1$ and $R^2$, which may be the same or different, represent, independently, hydrogen, $C_1-C_4$ alkyl, or $R^1$ and $R^2$ may form, taken together with the nitrogen atom they are linked to, a five-membered unsaturated or six-membered unsaturated or saturated monoheterocyclic ring, optionally containing one more heteroatom selected from nitrogen, oxygen and sulfur, or a five-membered saturated monoheterocyclic ring;

B represents a five-membered unsaturated or six-membered unsaturated or saturated monocarbocyclic or monoheterocyclic ring, optionally containing one or more heteroatom selected from nitrogen, oxygen and sulfur, or five-membered saturated monocarbocyclic or monoheterocyclic ring and the monocarbocycle or the monoheterocycle may be unsubstituted or substituted by one or more substituents selected from $C_1-C_4$ alkyl, halogen, $(CH_2)_m OR$, $(CH_2)_m NR^1 R^2$ in which m, R, $R^1$ and $R^2$ have the previously defined meanings;

when the symbol -------- represents a double bond

A represents oxygen, $CH$⁓$(CH=CH)_s$ ⁓$(CH_2)_n OR$, $CH$⁓$(CH=CH)_s$ ⁓$(CH_2)_n NR^1 R^2$, $CH$⁓$(CH=CH)_s$ ⁓$(CH_2)_p B$;

wherein

⁓, n, p, R, $R^1$, $R^2$ and B have the previously defined meanings and s represents 0 or 1;

L represents $[CH=C(R^3)]_s CH=NR^4$, $[CH=C(R^3)]_s CH_2 NHR^4$;

wherein the double bonds = have the E configuration;

s has the previously defined meaning;

$R^3$ represents hydrogen or $CH_3$ and $R^4$ represents $NHC(=N$⁓$R^5)NR^6 R^7$ or $OR^8$ wherein the symbol ⁓ has the previously defined meanings;

$R^5$ represents hydrogen, $C_1-C_4$ alkyl;

$R^6$, $R^7$, which may be the same or different, represent, independently, hydrogen or $C_1-C_4$ alkyl unsubstituted or substituted by $NR^9 R^{10}$ wherein $R^9$ and $R^{10}$, which may be the same or different, represent, independently, hydrogen or $C_1-C_4$ alkyl;

$R^5$, $R^6$, $R^7$, taken two by two may form, together with the heteroatom they are linked to, and where possible, a five-, six- or seven-membered monoheterocyclic ring;

$R^8$ represents hydrogen, $CH_3$, $C_2-C_6$ alkyl unsubstituted or substituted by $NR^9 R^{10}$ or $NHC(=NH)NH_2$.

wherein $R^9$ and $R^{10}$ have the previously defined meanings.

Where the compounds of formula (I) can exhibit tautomerism, the formula is intented to cover all tautomers; the invention includes within its scope, and whenever not otherwise specified, all the possible stereoisomers, Z and E isomers and optical isomers and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e. g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

The alkyl groups are branched or straight chain groups or cyclic groups.

The $C_1-C_4$ alkyl is preferably methyl, ethyl, n-propyl, iso-propyl, n-butyl, tert-butyl.

The $C_2-C_6$ alkyl is preferably ethyl, n-propyl, iso-propyl, n-butyl, n-pentyl, n-hexyl.

The R group is preferably hydrogen, methyl, ethyl, n-propyl, n-butyl, 2-aminoethyl, 3-aminopropyl, 2-dimethylaminoethyl, 3-dimethylaminopropyl, 2-(1-pyrrolidinylethyl), 3-(1-pyrrolidinylpropyl), 2-(4-morpholinoethyl), 3-(4-morpholinopropyl), 2-(1-piperazinylethyl), 3-(1-piperazinylpropyl), 2-(1-(4-methyl)piperazinylethyl), 3-(1-(4-methyl)piperazinylpropyl), 2-(1-imidazolylethyl), 3-(1-imidazolylpropyl).

The B group is preferably phenyl, 2-pyridyl, 3-pyridyl, 4-pyridyl, cyclopentyl, cyclohexyl.

The $NR^6R^7$ group is preferably amino, methylamino, dimethylamino, diethylamino, pyrrolidinyl, piperidinyl, 2-dimethylaminoetil, 2-diethylaminoetil.

$R^5$ and $R^6$ groups taken together with the heteroatom they are linked to, are preferably 2-imidazolin-2-yl, 1-methyl-2-imidazolin-2-yl, 1,4,5,6-tetrahydro-2-pyrimidinyl, 1-methyl-1,4,5,6-tetrahydro-2-pyrimidinyl.

Preferred examples of specific compounds according to the present invention are (1S,3aS,5S,7aR)-1-[(E)-guanidinoimino]methyl-5-phenyl-7a-methylperhydroinden-3a-ol (1S,3aS,5S,7aR)-1-[(E)-(2-imidazolin-2-yl)hydrazono]methyl-5-phenyl-7a-methylperhydroinden-3a-ol (1S,3aS,5S,7aR)-1-[(E)-1-methyl-(2-imidazolin-2-yl)hydrazono]methyl-5-phenyl-7a-methylperhydroinden-3a-ol (1S,3aS,5S,7aR)-1-[(E)-(1,4,5,6-tetrahydro-2-pyrimidinyl)hydrazono]-methyl-5-phenyl-7a-methylperhydroinden-3a-ol (1S,3aS,5S,7aR)-1-[(E)-hydroxyimino]methyl-5-phenyl-7a-methylperhydroinden-3a-ol (1S,3aS,5S,7aR)-1-[(E)-2-aminoethoxyimino]methyl-5-phenyl-7a-methylperhydroinden-3a-ol (1S,3aS,5S,7aR)-1-[(E)-3-aminopropoxyimino]methyl-5-phenyl-7a-methylperhydroinden-3a-ol (1S,3aS,5S,7aR)-1-[(E)-4-aminobutoxyimino]methyl-5-phenyl-7a-methylperhydroinden-3a-ol (1S,3aS,5S,7aR)-1-[(E)-2-dimethylaminoethoxyimino]methyl-5-phenyl-7a-methylperhydroinden-3a-ol (1S,3aS,5S,7aR)-1-[(E)-3-dimethylaminopropoxyimino]methyl-5-phenyl-7a-methylperhydroinden-3a-ol (1S,3aS,5S,7aR)-1-[(E)-4-dimethylaminobutoxyimino]methyl-5-phenyl-7a-methylperhydroinden-3a-ol (1S,3aS,5S,7aR)-1-[(E)-2-guanidinoethoxyimino]methyl-5-phenyl-7a-methylperhydroinden-3a-ol (1S,3aS,5S,7aR)-1-guanidinoaminomethyl-5-phenyl-7a-methylperhydroinden-3a-ol (1S,3aS,5S,7aR)-1-(2-aminoethoxyamino)methyl-5-phenyl-7a-methylperhydroinden-3a-ol (1S,3aS,5S,7aR)-1-(3-aminopropoxyamino)methyl-5-phenyl-7a-methylperhydroinden-3a-ol (1S,3aS,5S,7aR)-1-(2-dimethylaminoethoxyamino)methyl-5-phenyl-7a-methylperhydroinden-3a-ol (1S,3aS,5S,7aR)-1-(3-dimethylaminopropoxyamino)methyl-5-phenyl-7a-methylperhydroinden-3a-ol (1R, 3aS,5S,7aR)-1-[(E,E)-3-guanidinoimino-1-propenyl]-5-phenyl-methylperhydroinden-3a-ol (1R, 3aS,5S,7aR)-1-[(E,E)-3-(2-aminoethoxyimino)-1-propenyl]-5-phenyl-7a-methylperhydroinden-3a-ol (1R, 3aS,5S,7aR)-1-[(E,E)-3-(2-dimethylaminoethoxyimino)-1-propenyl]-5-phenyl-7a-methylperhydroinden-3a-ol (1R, 3aS,5S,7aR)-1-[(E)-3-guanidinoamino-1-propenyl]-5-phenyl-7a-methylperhydroinden-3a-ol (1R, 3 aS,5S,7aR)-1-[(E)-3-(2-aminoethoxyamino)-1-propenyl]-5-phenyl-7a-methylperhydroinden-3a-ol (1R, 3aS,5S,7aR)-1-[(E)-3-(2-dimethylaminoethoxyamino)-1-propenyl]-5-phenyl-7a-methylperhydroinden-3a-ol (1R, 3aS,5S,7aR)-1-[(E,E)-2-methyl-3-guanidinoimino-1-propenyl]-5-phenyl-7a-methylperhydroinden-3a-ol (1R, 3aS,5S,7aR)-1-[(E,E)-2-methyl-3-(2-aminoethoxyimino)-1-propenyl]-5-phenyl-7a-methylperhydroinden-3a-ol (1R, 3aS,5S,7aR)-1-[(E,E)-2-methyl-3-(2-dimethylaminoethoxyimino)-1-propenyl]-5-phenyl-7a-methylperhydroinden-3a-ol (1R,3aS,5S,7aR)-1-[(E)-2-methyl-3-guanidinoimino-1-propenyl]-5-phenyl-7a-methylperhydroinden-3a-ol (1R,3aS,5S,7aR)-1-[(E)-2-methyl-3-(2-aminoethoxyamino)-1-propenyl]-5-phenyl-7a-methylperhydroinden-3a-ol (1R,3aS,5S,7aR)-1-[(E)-2-methyl-3-(2-dimethylaminoethoxyamino)-1-propenyl]-5-phenyl-7a-methylperhydroinden-3a-ol and the corresponding (5S)-5-(3-hydroxyphenyl), (5S)-5-(4-hydroxyphenyl), (5S)-5-(3-hydroxymethylphenyl), (5S)-5-(4-hydroxymethylphenyl), (5S)-5-(3-methylphenyl), (5S)-5-(4-methylphenyl), (5S)-5-[3-(2-dimethylaminoethoxy)phenyl], (5S)-5-[4-(2-dimethylaminoethoxy)phenyl], (5S)-5-[3-(2-dimethylaminoethoxymethyl)phenyl], (5S)-5-[4-(2-dimethylaminoethoxymethyl)phenyl], (5S)-5-(2-hydroxyethoxy), (5S)-5-(3-hydroxypropoxy), (5S)-5-[2-(2-dimethylaminoethoxy)ethoxy], (5S)-5-[3-(2-dimethylaminoethoxy)propoxy], (5R)-5-(3-hydroxypropyl), (5R)-5-(3-dimethylaminopropyl), (5S)-5-(4-hydroxybutyl), (5S)-5-(4-dimethylaminobutyl), (5R)-5-benzyl, (5R)-5-(3-hydroxybenzyl), (5R)-5-(4-hydroxybenzyl), (5R)-5-(3-hydroxymethylbenzyl), (5R)-5-(4-hydroxymethylbenzyl), (5S)-[(Z)-4-hydroxy-1-butenyl)], (5S)-[(Z)-4-dimethylamino-1-butenyl)], 5-[(Z)-3-hydroxypropyliden], 5-[(Z)-3-dimethylaminopropyliden], 5-[(Z)-3-(2-dimethylaminoethoxy)propyliden], 5-[(Z)-benzyliden], (5S)-cyclohexyl, (5R)-cyclohexylmethyl, (5S)-3-pyridyl, (5S)-4-pyridyl, (5S)-5-(4-cis-hydroxy-r-1-cyclohexyl), (5S)-5-(4-transhydroxy-r-1-cyclohexyl) derivatives of the compounds mentioned above; and the corresponding 5-[(E) isomers of the 5-[(Z) derivatives mentioned above.

The invention furthermore provides a process for the preparation of compounds of general formula (I), which comprises a condensation reaction of compounds of formula (II)

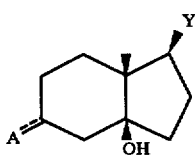

(II)

wherein Y represents [CH=C(R³)]ₛCHO, in which A, ........., R³ and s are as above defined and when s is 1 the double bond ═ is in the E configuration, with a compound of general formula (III) and (IV)

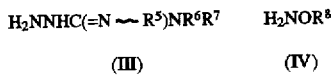

wherein R⁵, R⁶, R⁷ and R⁸ are as above defined, to give compounds of general formula (I). Compounds (III) and (IV) can be used as the free base or in the form of a salt with an acid such as, e.g., hydrochloric, hydrobromic, carbonic, oxalic, hydriodic or sulfuric acid. The reaction can be carried out in a solvent, such as ethanol, methanol, acetonitrile, dioxane, tetrahydrofuran, water or a mixture of said solvents, at a temperature between 0° C. and the boiling point of the above mentioned solvents or of their mixtures. To the reaction mixtures, additional salts, such as, e.g., NaH₂PO₄, Na₂HPO₄, NaOAc, can be added as well as acids such as, e.g., hydrochloric, hydrobromic, sulfuric, acetic, phosphoric, and bases such as, e.g., sodium or potassium hydroxide, to maintain the desired pH.

Compounds of general formula (I) can be converted into other compounds of general formula (I) by known methods.

Compounds of general formula (I) where L is [CH=C(R³)]ₛCH₂NHR⁴, wherein R³, R⁴ and s have the meanings above defined and when s is 1 the double bond ═ is the E configuration, can be prepared from the corresponding compounds of general formula (I) where L is [CH=C(R³)]ₛCH=NR⁴, wherein R³, R⁴ and s have the meanings above defined and the double bond ═ is the E configuration when s is 1, by means of a reduction reaction with hydrogen in the presence of a suitable catalyst or with metal hydrides. The reduction reactions can be carried out using hydrogen in the presence of a catalyst, such as palladium on charcoal, platinum dioxide or Raney-nickel at a pressure between atmospheric and 10 atm.; the catalytic reduction reaction can also be performed in hydrogen transfer conditions using, for example, ammonium formate or sodium hypophosphite in the presence of one of the above said catalysts. The reduction reactions can also be carried out with metal hydrides such as, e.g., sodium borohydride, sodium cyanoborohydride, borane. The reduction reactions can be carried out in a solvent, such as ethanol, methanol, dioxane, tetrahydrofuran, water or a mixture of said solvents, at a temperature between 0° C. and the boiling point of the solvents mentioned above or of their mixtures. To the reaction mixtures, additional acids, e.g., hydrochloric, hydrobromic, sulfuric, acetic, phosphoric acid, and bases such as, e.g., sodium or potassium hydroxide, can be added to maintain the desired pH.

Compounds of general formula (I) where L is [CH=C(R³)]ₛCH=NOR⁸ wherein R³ and s have the meanings above defined and when s is 1 the double bond ═ is the E configuration, and R⁸ contains a guanidino group can be prepared from the corresponding compounds of general formula (I) where L is [CH=C(R³)]ₛCH=NR⁴, wherein R³ and s have the meanings above defined and R⁴ contains a primary amino group by reaction, for example, with 1-amidino-3,5-dimethylpyrazole or S-methyl isothiourea, both as free bases or as salts. The reaction can be carried out in a solvent, such as ethanol, methanol, dioxane, acetonitrile, tetrahydrofuran, water or a mixture of said solvents, at a temperature between 0° C. and the boiling point of the solvents mentioned above or of their mixtures.

Compounds of general formula (II) where A and ........ have the meanings above defined and Y is [CH=C(R³)]ₛCHO wherein R³ has the meanings above defined, s is 1 and the double bond is the E configuration can be prepared from the corresponding compounds of general formula (II) where A and ........ have the meanings above defined and Y is [CH=C(R³)]ₛCHO wherein s is 0, for example, by reaction with trimethyl 2-phosphonoacetate, triethyl 2-phosphonoacetate, trimethyl 2-phosphonopropionate or triethyl 2-phosphonopropionate, in the presence of a base, for example sodium hydride or di-iso-propylethylamine in the presence of lithium chloride, followed by reduction of the α,β-unsaturated ester function to the corresponding allylic alcohol, for example with di-iso-butylaluminum hydride, and subsequent allylic oxidation to the α,β-unsaturated aldehyde, for example with manganese dioxide; by reaction with diethylphosphonoacetaldehyde cyclohexylimine or with 2-diethylphosphonopropionaldehyde cyclohexylimine in the presence of a base, for example sodium hydride, followed by hydrolysis of the adduct, according to a general procedure described by Nagata W. e Hayase Y. in *J. Chem. Soc. C*, 1969, 460; by reaction with the adduct of acetaldehyde tert-butylimine or propionaldehyde tert-butylimine with diethyl chlorophosphate in the presence of a base, for example sodium hydride, followed by acid hydrolysis, according to a general procedure described by Meyers A. I. et al. in *J. Org. Chem.*, 1978, 43, 3788.

Compounds of general formula (II) where Y represents [CH=C(R³)]ₛCHO wherein s is 0, A and ........ have the above defined meanings can be prepared by known oxidation reactions of the corresponding compounds of general formula (V)

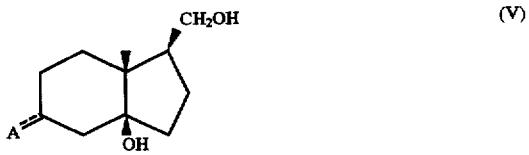

where A and ........ have the above defined meanings, with chromium trioxide in pyridine or in sulfuric acid and acetone, pyridinium dichromate, pyridinium chlorochromate, dimethylsulfoxide with oxalyl chloride and triethylamine, o-iodoxybenzoic acid in dimethylsulfoxide.

Compounds of general formula (V) where ........ represents a single bond and A represents (CH=CH)ₘ⁓(CH₂)ₙOR, (CH=CH)ₘ⁓(CH₂)ₙNR¹R² and (CH=CH)ₘ⁓(CH₂)ₚB in which m is zero and R, R¹, R², B and n have the meanings above defined and p is 1 or 2, can be prepared from the compounds of general formula (V) where ........ represents a double bond and A represents CH⁓(CH₂)ₙ₋₁OR, CH⁓(CH₂)ₙ₋₁NR¹R², CH⁓(CH₂)ₚB wherein p means 0 or 1, R, R¹, R² and B have the above defined meanings and 2≦n≦5 by means of one of the catalytic hydrogenation reported in the literature using, for example, hydrogen and Pd on charcoal, PtO₂, Raney-nickel as catalyst or by hydrogen transfer reactions using, for example, ammonium formate or sodium hypophosphite in the presence of one of the above cited catalysts.

Compounds of general formula (V) where ........ represents a single bond and A represents (CH=CH)ₘ

‌‌(CH$_2$)$_n$OR, (CH=CH)$_m$‌‌(CH$_2$)$_n$NR$^1$R$^2$ and (CH=CH)$_m$‌‌(CH$_2$)$_p$B wherein R, R$^1$, R$^2$, B, n and p have the above defined meanings and m is 1 or 2, can be prepared from (1S,3aS,5S,7aR)-1-hydroxymethyl-5-formyl-7a-methylperhydroinden-3a-ol by reaction with a compound of general formula Ph$_3$P$^+$CH$_2$(CH=CH)$_s$(CH$_2$)$_n$OR, Ph$_3$P$^+$CH$_2$(CH=CH)$_s$(CH$_2$)$_n$NR$^1$R$^2$ or Ph$_3$P$^+$CH$_2$(CH=CH)$_s$(CH$_2$)$_p$B in which R, R$^1$, R$^2$, B, n, p and s have the above defined meanings, in the presence of a base such as, for example, sodium hydride, potassium tert-butoxide or n-butyllithium.

Compounds of general formula (V) where ‌‌‌‌‌‌‌‌ represents a single bond and A represents (CH=CH)$_m$ ‌‌(CH$_2$)$_n$OR where m is zero, R represents hydrogen and n is 1, can be prepared from (1S,3aS,5S,7aR)-1-hydroxymethyl-5-formyl-7a-methylperhydroinden-3a-ol by reaction with a reducing agent such as, for example, sodium borohydride.

Compounds of general formula (V) where ‌‌‌‌‌‌‌‌ represents a single bond and A represents (CH=CH)$_m$ ‌‌(CH$_2$)$_n$OR where m, n and R have the above defined meanings with the proviso that R is different from hydrogen can be prepared from the compounds of general formula (V) where ‌‌‌‌‌‌‌‌ represents a single bond and A represents (CH=CH)$_m$‌‌(CH$_2$)$_n$OR wherein m and n are as above defined and R represents hydrogen, by reaction with a compound WR where R has the above defined meanings with the exclusion of hydrogen and W represents an electron-withdrawing group such as, for example, halogen, methanesulfonyl or p-toluensulfonyl, in the presence of a base such as, for example, sodium or potassium hydride; in this sequence of reactions the hydroxy group present in the hydroxymethyl group in position 1 Is protected, for example as acetate, tert-butyldimethylsilyl ether or tetrahydropyranyl ether, before the alkylating reaction.

Compounds of general formula (V) where ‌‌‌‌‌‌‌‌ represents a single bond and A represents (CH=CH)$_m$ ‌‌(CH$_2$)$_n$NR$^1$R$^2$ where m is 0, n is 1 and R$^1$ and R$^2$ have the above defined meanings, can be prepared from (1S,3aS,5S,7aR)-1-hydroxymethyl-5-formyl-7a-methylperhydro-inden-3a-ol by reaction with a compound of general formula HNR$^1$R$^2$ in the presence of a reducing agent such as, for example, sodium borohydride or sodium cyanoborohydride in the presence, if necessary, of acids, such as hydrochloric or acetic, or salts, such as sodium acetate or sodium dihydrogenphosphate.

(1S,3aS,5S,7aR)-1-Hydroxymethyl-5-formyl-7a-methylperhydroinden-3a-ol can be prepared from (1S,3aS,7aR)-1-hydroxymethyl-3a-hydroxy-7a-methylperhydroinden-5-one for example using one of the following methods: by reaction with methoxymethyltriphenylphosphonium chloride or bromide in the presence of a base such as, for example, sodium hydride, potassium tert-butoxide, n-butyllithium followed by acid hydrolysis of the intermediate methyl enol ether and purification; by reaction with methyltriphenylphosphonium chloride or bromide in the presence of a base such as, for example, sodium hydride, potassium tert-butoxide, n-butyllithium followed by hydroboration-oxidation of the methyliden derivative, for example with borane and hydrogen peroxide or sodium perborate, purification of the mixture of the epimeric alcohols and oxidation of the hydroxymethyl derivative by means of one of the reagents reported in the literature such as, for example chromium trioxide in pyridine or in sulfuric acid and acetone, pyridinium dichromate, pyridinium chlorocromate, dimethylsulfoxide with oxalyl chloride and triethylamine, o-iodoxybenzoic acid in dimethylsulfoxide; in this sequence of reactions the hydroxy group present in the hydroxymethyl group in position 1 is protected, for example as acetate, tert-butyldimethylsilyl ether or tetrahydropyranyl ether, before the olefinations reaction.

Compounds of general formula (V) where ‌‌‌‌‌‌‌‌ represents a single bond and A represents (CH=CH)$_m$ ‌‌(CH$_2$)$_p$B wherein B represents an unsaturated five-or six-membered monocarbocycle or monoheterocycle and m and p mean 0, can be prepared from compounds of general formula (VI)

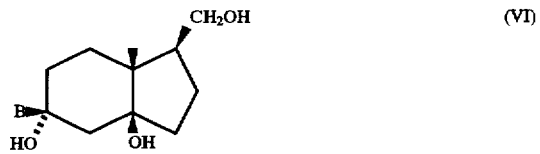

by hydrogenolysis of the allylic-or benzylic-type alcohol. Such reactions can be carried out by catalytic hydrogenation using, for example, catalysts such as Pd on charcoal, PtO$_2$, Raney-nickel in the presence, if necessary, of acids such as, for example, hydrochloric or perchloric acid, or by hydrogen transfer reactions using, for example, ammonium formate or sodium hypophosphite in the presence of one of the above cited catalysts.

Compounds of general formula (VI) can be prepared from (1S,3aS,7aR)-1-hydroxymethyl-3a-hydroxy-7a-methylperhidroinden-5-one, by reaction, for example, with a compound of general formula BM, where B has the meanings above described and N[means, for example, Li, MgBr, MgCl, MgI, CeCl$_2$. The reaction can be carried out in a solvent such as, for example, diethyl ether, tetrahydrofuran, dioxane, toluene or in a mixture of said solvents, at a temperature between −100° C. and the boiling point of the solvents mentioned above or of their mixtures.

Compounds of general formula (V) where ‌‌‌‌‌‌‌‌ represents a single bond and A represents (CH=CH)$_m$ ‌‌(CH$_2$)$_p$B wherein B represents a saturated five-or six-membered monocarbocycle or monoheterocycle and m and p mean 0, can be prepared from compounds of general formula (V) where ‌‌‌‌‌‌‌‌ represents a single bond and A represents (CH=CH)$_m$‌‌(CH$_2$)$_p$B wherein B represents an unsaturated five-or six-membered monocarbocycle or monoheterocycle and m and p are 0 by catalytic hydrogenation using, for example, catalysts such as Pd on charcoal, PtO$_2$, Raney-nickel at pressure between atmospheric and 10 atm., in a solvent, such as, for example, methanol, ethanol, water, ethyl acetate, tetrahydrofuran or in a mixture of said solvents, at a temperature between 0° C. and the boiling point of the solvents or of their mixtures, in the presence, if necessary, of acids such as, for example, hydrochloric or perchloric acid, or by hydrogen transfer reactions using, for example, ammonium formate or sodium hypophosphite in the presence of one of the above mentioned catalysts, in one of the above mentioned solvents or their mixtures.

Compounds of general formula (V) where ‌‌‌‌‌‌‌‌ represents a single bond and A represents OH, that is (1S,3aS,5S,7aR)-1-hydroxymethyl-7a-methylperhidroinden-3a,5-diol can be prepared from (1S,3aS,7aR)-1-hydroxymethyl-3a-hydroxy-7a-methylperhydroinden-5-one, by reaction with a reducing agent such as, for example, sodium borohydride, sodium cyanoborohydride, lithium aluminumhydride, L-Selectride®, K-Selectride® followed by purification from the (5R) isomer, for example by column chromatography.

Compounds of general formula (V) where ‌‌‌‌‌‌‌‌ represents a single bond and A represents O(CH$_2$)$_q$OR, $O(CH_2)_qNR^1R_2$, $O(CH_2)_rB$, where in R, $R^1$, $R^2$, B, q and r have the above defined meanings provided that R is different from hydrogen, can be prepared from (1S,3aS,5S,7aR)-1-hydroxymethyl-7a-methylperhidroinden-3a, 5-diol having the primary hydroxyl group protected, for example as acetate, by reaction with compounds of general formula $W(CH_2)_qOR$, $W(CH_2)_qNR^1R^2$, $W(CH_2)_rB$ where R, $R^1$, $R^2$, B, q and r have the above defined meanings provided that R is different from hydrogen and W represents an electron-withdrawing group such as, for example, halogen, methane-sulfonyl or p-toluensulfonyl, in the presence of a base such as, for example, sodium or potassium hydride and final deprotection of the protected primary hydroxyl group.

Compounds of general formula (V) where ------- represents a single bond and A represents $O(CH_2)_qOR$ wherein R and q have the above defined meanings provided that R is different from hydrogen, can also be prepared from compounds of general formula (V) where ------- represents a single bond and A represents $O(CH_2)_qOR$ where R is hydrogen and q has the above defined meanings, by reaction with compounds of general formula WZ, where W has the above defined meanings and Z represents $C_1$–$C_4$ alkyl unsubstituted or substituted with $NR^1R^2$, in which $R^1$ and $R^2$ have the above defined meanings, in the presence of a base such as, for example, sodium or potassium hydride.

Compounds of general formula (V) where ------- represents a single bond and A represents $O(CH_2)_qOR$ wherein R represents hydrogen and q has the above defined meanings, can be prepared from (1S,3aS,5S,7aR)-1-hydroxymethyl-7a-methylperhidroinden-3a, 5-diol by reaction with a ω-halogenoaldehyde diakylacetal, ω-halogenoester or ω-halogenoalcohol with the alcoholic group protected, in the presence of a base such as, for example, sodium or potassium hydride, followed by acid hydrolysis of the protecting group of the hydroxyl function or by deprotection of the aldehydic group and reduction of the aldehyde or ester function to the corresponding alcohol, for example with sodium borohydride or lithium aluminum-hydride.

Compounds of general formula (V) where ------- represents a double bond and A represents CH ᴡ(CH=CH)$_s$ ᴡ(CH$_2$)$_n$OR, CH ᴡ(CH=CH)$_s$ ᴡ(CH$_2$)$_n$NR$^1$R$^2$ e CH ᴡ(CH=CH)$_s$ ᴡ(CH$_2$)$_p$B wherein R, $R^1$, $R^2$, B, n, p and s have the above defined meanings can be prepared from (1S,3aS,7aR)-1-hydroxymethyl-3a-hydroxy-7a-methylperhydroinden-5-one, by reaction wi formula Ph$_3$P$^+$CH$_2$ᴡ(CH=CH)$_s$ᴡ(CH$_2$)$_n$OR, Ph$_3$P$^+$CH$_2$ᴡ(CH=CH)$_s$ᴡ(CH$_2$)$_n$OR, Ph$_3$P$^+$CH$_2$ᴡ(CH=CH)$_s$ ᴡ(CH$_2$)$_p$B where R, $R^1$, $R^2$, B, n, p and s have the above defined meanings, in the presence of a base such as, for example, sodium hydride or n-butyllithium.

(1S,3aS,7aR)-1-Hydroxymethyl-3a-hydroxy-7a-methylperhydroinden-5-one can be prepared from 3aS,7aS)-3a-idrossi-7a-metilperhydroinden-1,5-dione (Hajos Z. G. and Parrish D. R. in *J. Org. Chem.*, 1974, 39, 1615) for example with one of the following methods: by reaction with methoxymethyltriphenylphosphonium chloride or bromide in the presence of a base such as, for example, sodium hydride, potassium tert-butoxide, n-butyllithium, followed by acid hydrolysis of the intermediate methyl enol ether and reduction of the aldehyde for example with sodium borohydride; by reaction with methyltriphenylphosphonium chloride or bromide in the presence of a base such as, for example, sodium hydride, potassium tert-butoxide, n-butyllithium, followed by hydroboration-oxidation of the methyliden derivative, for example with borane and hydrogen peroxide or sodium perborate: the (1S) isomer can be purified from the (1R) isomer for example by column chromatography; the more reactive keto group in position 5 can be protected, for example as ethyleneketal, propyleneketal, ethylenedithioketal or propylenedithioketal and deprotected, when necessary, to give the keto group.

In all the transformations mentioned above the functional groups optionally present in the molecule and interfering with the reagents are protected by known methods and deprotected when necessary and possible by methods known in the literature to give compounds included in the general formulas (I), (II), (V) e (VI).

Compounds of general formula (III)and (IV) are known compounds, generally commercially available, or obtainable from known compounds by known methods.

Said transformations are only examples of well established procedures described in Organic Chemistry (see for example: J. March "Advanced Organic Chemistry", J. Wiley & Sons, 1985; D. Barton and W. D. Ollis "Comprehensive Organic Chemistry", Pergamon Press, 1979) well known to those skilled in the art.

The following examples illustrate the invention without limiting it.

EXAMPLE 1

(1S,3aS,5S,7aR)-1-[(E)-Guanidinoimino]methyl-5-phenyl-7a-methylperhydroinden-3a-ol (I-aa)

A solution of 0.57 g of (1S,3aS,5S,7aR)-1-formyl-5-phenyl-7a-methylperhydroinden-3a-ol and 1.50 g of aminoguanidine hydrogencarbonate in 30 ml of 0.01N hydrochloric acid and 80 ml of dioxane was kept at room temperature for 3 days and then evaporated to dryness under reduced pressure. The crude product was purified by flash-chromatography (SiO$_2$) using chloroform/methanol/28% ammonium hydroxide 78/20/2 as the eluant. The fractions containing the title compound were collected and evaporated to dryness. The residue was triturated with ethanol/ethyl acetate to give 0.48 g of the title compound (I-aa) as a white solid.

$^1$H NMR (300 MHz, DMSO-d$_6$, ppm from TMS): 0.73 (3H, s); 1.32–2.42 (11H, m); 2.71 (1H, m); 4.01 (1H, s); 5.20–5.81 (4H, bb); 7.18–7.28 (5H, m); 7.43 (1H, d).

Using the same procedure described in Ex. 1 and starting from the appropriate aldehyde and aminoguanidine hydrogencarbonate, the following compounds were obtained:

(1S,3aS,5R,7aR)-1-[(E)-Guanidinoimino]methyl-5-benzyl-7a-methylperhydroinden-3a-ol (I-ab)

$^1$H NMR (300 MHz, DMSO-d$_6$, ppm from TMS): 0.78 (3H, s); 1.10–1.70 (9H, m); 1.96 (2H, m); 2.18 (1H, m); 2.50 (2H, s); 4.02 (1H, s); 5.20–5.82 (4H, bb); 7.12–7.28 (5H, m); 7.43 (1H, d).

(1S,3aS,5S,7aR)-1-[(E)-Guanidinoimino]methyl-5-[(E)-4-dimethylamino-1-butenyl]-7a-methylperhydroinden-3a-ol (I-ac)

$^1$H NMR (300 MHz, DMSO-d$_6$, ppm from TMS): 0.72 (3H, s); 1.45–2.55 (16H, m); 2.23 (6H, s); 4.01 (1H, s); 5.20–5.80 (4H, bb, and 2H, m); 7.43 (1H, d).

(1S,3aS,5S,7aR)-1-[(E)-Guanidinoimino]methyl-5-cyclohexyl-7a-methylperhydroinden-3a-ol (I-ad)

$^1$H NMR (300 MHz, DMSO-d$_6$, ppm from TMS): 0.72 (3H, s); 0.80–1.80 (20H, m); 1.98 (2H, m); 2.28 (1H, m); 4.01 (1H, s); 5.20–5.81 (4H, bb); 7.42 (1H, d).

EXAMPLE 2

(1R,3aS,5S,7aR)-1-[(E,E)-3-Guanidinoimino-1-propenyl]-5-phenyl-7a-methylperhydroinden-3a-ol (I-ae)

The title compound (I-ae) was obtained as a white solid using the procedure described in Ex. 1 but carrying out the reaction at pH 3.0 adjusted at that value by means of 0.1N HCl.

$^1$H-NMR (300 MHz, DMSO-d$_6$, ppm from TMS): 0.72 (3H, s); 1.40–1.80 (8H, m); 2.26 (2H, m); 2.75 (1H, m); 2.81 (1H, m); 3.98 (1H, s); 5.40–5.80 (4H, bb); 5.88 (1H, dd); 6.05 (1H, dd); 7.10–7.30 (5H, m); 7.61 (1H, d).

Using the same procedure of Ex. 2 and stating from the appropriate aldehyde and aminoguanidine hydrogencarbonate, the following compounds were obtained:

(1R,3aS,5S,7aR)-1-[(E,E)-2-Methyl-3-guanidinoimino-1-propenyl]-5-phenyl-7a-methylperhydroinden-3a-ol (I-af)

$^1$H-NMR (300 MHz, CD$_3$OD, ppm from TMS): 0.85 (3H, s); 1.45–1.80 (8H, m); 1.82 (3H, d); 2.05–2.30 (2H, m); 2.75 (2H, m); 6.15 (1H, d); 7.10–7.30 (5H, m); 7.65 (1H, s).

(1R,3aS,5S,7aR)-1-[(E,E)-3-Guanidinoimino-1-propenyl]-5-(4-hydroxyphenyl)-7a-methylperhydroinden-3a-ol (I-ag)

$^1$H-NMR (300 MHz, DMSO-d$_6$, ppm from TMS): 0.76 (3H, s); 1.40–1.80 (8H, m); 2.25 (2H, m); 2.52 (1H, m); 2.81 (1H, m); 3.98 (1H, s); 5.40–5.80 (4H, bb); 5.88 (1H, dd); 6.05 (1H, dd); 6.78 (2H, d); 7.08 (2H, d); 7.61 (1H, s).

(1R,3aS,5S,7aR)-1-[(E,E)-3-Guanidinoimino-1-propenyl]-5-cyclohexyl-7a-methylperhydroinden-3a-ol (I-ah)

$^1$H-NMR (300 MHz, DMSO-d$_6$, ppm from TMS): 0.72 (3H, s); 0.80–1.75 (20H, m); 2.01 (2H, m); 2.19 (1H, m); 3.98 (1H, bs); 5.40–5.80 (4H, bb); 5.88 (1H, dd); 6.05 (1H, dd); 7.61 (1H, d).

(1R,3aS,5S,7aR)-1-[(E,E)-2-Methyl-3-guanidinoimino-1-propenyl]-5-cyclohexyl-7a-methylperhydroinden-3a-ol (I-ai)

$^1$H-NMR (300 MHz, CD$_3$OD, ppm from TMS): 0.85 (3H, s); 0.90–1.80 (20H, m); 1.88 (3H, s); 2.05–2.30 (2H, m); 2.80 (1H, m); 6.18 (1H, d); 7.69 (1H, s).

EXAMPLE 3

(1S,3aS,5S,7aR)-1-[(E)-(2-Imidazolin-2-yl)hydrazono]methyl-5-phenyl-7a-methylperhydroinden-3a-ol hydrobromide (I-aj)

To a solution of 0.93 g of 2-hydrazino-2-imidazoline hydrobromide in 45 ml of water and 30 ml of dioxane a solution of 0.89 g of (1S,3aS,5S,7aR)-1-formyl-5-phenyl-7a-methylperhydroinden-3a-ol in 30 ml of dioxane was added dropwise at room temperature and the mixture was stirred for 2 hrs. The solution was evaporated to dryness under reduced pressure and the residue was ground with ethanol/water then with ethanol to give 0.78 g of the title compound (I-al) as a white solid.

$^1$H-NMR (300 MHz, DMSO-d$_6$, ppm from TMS): 0.76 (3H, s); 1.45–2.53 (11H, m); 2.75 (1H, m); 4.01 (4H, s); 4.17 (1H, s); 7.18–7.28 (5H, m); 7.53 (1H, d); 7.70–8.80 (2H, bb); 11.80 (1H, bb).

Using the same procedure described in Ex. 3 and starting from the appropriate aldehyde and hydrazino derivatives, the following compounds were obtained:

(1S,3aS,5S,7aR)-1-[(E)-(1-Methyl-2-imidazolin-2-yl)hydrazono]-methyl-5-phenyl-7a-methylperhydroinden-3a-ol hydriodide (I-ak)

$^1$H-NMR (300 MHz, DMSO-d$_6$, ppm from TMS): 0.76 (3H, s); 1.40–2.55 (11H, m); 2.75 (1H, m); 3.10 (3H, s); 3.63 (4H, s); 4.01 (1H, s); 7.18–7.28 (5H, m); 7.54 (1H, d); 7.70–8.70 (1H, bb); 11.60 (1H, bb).

(1S,3aS,5S,7aR)-1-[(E)-(1,4,5,6-Tetrahydro-2-pyrimidinyl)hydrazono]methyl-5-phenyl-7a-methylperhydroinden-3a-ol hydriodide (I-al)

$^1$H-NMR (300 MHz, DMSO-d$_6$, ppm from TMS): 0.76 (3H, s); 1.40–2.56 (13H, m); 2.75 (1H, m); 3.25 (4H, m); 4.01 (1H, s); 7.18–7.28 (5H, m); 7.57 (1H, d); 7.90 (2H, bb); 11.10 (1H, bb).

EXAMPLE 4

(1S,3aS,5S,7aR)-1-[(E)-2-Aminoethoxyimino]methyl-5-phenyl-7a-methylperhydroinden-3a-ol (I-am)

To a solution of 6.30 g of 0.12 g of 2-aminoethoxyamine dihydrochloride, 0.28 g of sodium acetate in 2 ml of dioxane and 1 ml of water was made aid to pH 4.5 with 3N HCl. A solution of 0.20 g of (1S,3aS,5S,7aR)-1-formyl-5-phenyl-7a-methylperhydroinden-3a-ol in 1 ml of dioxane and 0.5 ml of water was added dropwise at room temperature. After 1 hr the solution was alkalinized with 10% aqueous Na$_2$CO$_3$ and extracted with ethyl acetate. The organic layer was dried over anhydrous sodium sulfate and evaporated to dryness. The crude product was ground with diethyl ether to give 0.17 g of the title compound (I-am) as a white solid.

$^1$H-NMR (300 MHz, CD$_3$OD, ppm from TMS): 1.00 (3H, s); 1.45–1.93 (9H, m); 2.15 (1H, m); 2.43 (1H, m); 2.73 (1H, m); 2.86 (2H, m); 3.98 (2H, m); 7.10–7.30 (5H, m); 7.61 (1H, d).

Using the same procedure described in Ex. 4 and starting from the appropriate aldehyde and hydroxylamine derivatives, the following compounds were obtained (when necessary the compounds were purified by flash chromatography):

(1S,3aS,5S,7aR)-1-[(E)-Hydroxyimino]methyl-5-phenyl-7a-methylperhydroinden-3a-ol (I-an)

$^1$H-NMR (300 MHz, CDCl$_3$, ppm from TMS): 1.05 (3H, s); 1.40–2.55 (11H, m); 2.72 (1H, m); 7.10–7.30 (5H, m); 7.65 (1H, d).

(1S,3aS,5S,7aR)-1-[(E)-3-Aminopropoxyimino]methyl-5-phenyl-7a-methylperhydroinden-3a-ol (I-ao)

$^1$H-NMR (300 MHz, CD$_3$OD, ppm from TMS): 1.00 (3H, s); 1.45–2.00 (10H, m); 2.15 (2H, m); 2.43 (1H, m); 2.73 (1H, m); 2.86 (2H, m); 3.98 (2H, m); 7.10–7.30 (5H, m); 7.65 (1H, d).

(1S,3aS,5S,7aR)-1-[(E)-2-Dimethylaminoethoxyimino]methyl-5-phenyl-7a-methylperhydroinden-3a-ol (I-ap)

$^1$H-NMR (300 MHz, CD$_3$OD, ppm from TMS): 1.02 (3H, s); 1.45–1.92 (8H, m); 2.15 (1H, m); 2.31 (6H, s); 2.41 (2H, m); 2.62 (2H, m); 2.73 (1H, m); 4.12 (2H, m); 7.10–7.30 (5H, m); 7.56 (1H, d).

(1S,3aS,5S,7aR)-1-[(E)-3-Dimethylaminopropoxyimino]methyl-5-phenyl-7a-methylperhydroinden-3a-ol oxalate (I-aq)

$^1$H-NMR (300 MHz, CD$_3$OD, ppm from TMS): 1.00 (3H, s); 1.45–2.50 (13H, m); 2.73 (1H, m); 2.88 (6H, s); 3.20 (2H, m); 4.15 (2H, m); 7.10–7.30 (5H, m); 7.57 (1H, d).

(1R,3aS,5S,7aR)-1-[(E,E)-2-Methyl-3-(2-aminoethoxyimino)]-1-propenyl]-5-phenyl-7a-methylperhydroinden-3a-ol oxalate (I-ar)

$^1$H-NMR (300 MHz, CD$_3$OD, ppm from TMS): 0.86 (3H, s); 1.45–2.50 (10H, m); 1.73 (3H, s); 2.73 (2H, m); 3.20 (2H, m); 4.18 (2H, m); 6.15 (1H, d); 7.10–7.30 (5H, m); 7.67 (1H, s).

(1R,3aS,5S,7aR)-1-[(E,E)-2-Methyl-3-(2-dimethylaminoethoxyimino)-1-propenyl]-5-phenyl-7a-methylperhydroinden-3a-ol oxalate (I-as)

¹H-NMR (300 MHz, CD₃OD, ppm from TMS): 0.86 (3H, s); 1.45–2.50 (10H, m); 1.73 (3H, s); 2.73 (2H, m); 2.90 (6H, s); 3.43 (2H, m); 4.15 (2H, m); 6.15 (1H, d); 7.10–7.30 (5H, m); 7.65 (1H, s).

(1S,3aS,5S,7aR)-1-[(E)-2-Aminoethoxyimino]methyl-5-(3-hydroxyphenyl)-7a-methylperhydroinden-3a-ol (I-at)

¹H-NMR (300 MHz, CDCl₃, ppm from TMS): 0.98 (3H, s); 1.41–2.00 (8H, m); 2.11 (1H, m); 2.30 (1H, m); 2.45 (1H, m); 2.65 (3H, m); 4.08 (2H, m); 6.65 (3H, m); 7.13 (1H, m); 7.56 (1H, d).

(1S,3aS,5S,7aR)-1-[(E)-2-Dimethylaminoethoxyimino]methyl-5-(3-hydroxyphenyl)-7a-methylperhydroinden-3a-ol (I-au)

¹H-NMR (300 MHz, CDCl₃, ppm from TMS): 0.98 (3H, s); 1.41–2.00 (8H, m); 2.11 (1H, m); 2.30 (6H, s and 1H, m); 2.45 (1H, m); 2.65 (3H, m); 4.15 (2H, m); 6.65 (3H, m); 7.13 (1H, m); 7.55 (1H, d).

(1R,3aS,5S,7aR)-1-[(E,E)-2-Methyl-3-(2dimethylaminoethoxyimino)-1-propenyl]-5-(3-hydroxyphenyl)-7a-methylperhydroinden-3a-ol oxalate (I-av)

¹H-NMR (300 MHz, CD₃OD, ppm from TMS): 0.85 (3H, s); 1.45–2.50 (10H, m); 1.84 (3H, s); 2.65 (1H, m); 2.80 (1H, m); 2.90 (6H, s); 3.40 (2H, m); 4.15 (2H, m); 6.15 (1H, d); 6.65 (3H, m); 7.15 (1H, m); 7.67 (1H, s).

(1S,3aS,5S,7aR)-1-[(E)-2-Aminoethoxyimino]methyl-5-(4-hydroxyphenyl)-7a-methylperhydroinden-3a-ol (I-aw)

¹H-NMR (300 MHz, DMSO-d₆, ppm from TMS): 0.88 (3H, s); 1.30–1.72 (8H, m); 2.02 (1H, m); 2.25 (2H, m); 2.43 (2H, m); 2.52 (1H, m); 3.92 (2H, m); 4.30 (1H, s); 6.62 (2H, d); 7.00 (2H, d); 7.42 (1H, d); 9.10 (1H, s).

(1S,3aS,5S,7aR)-1-[(E)-2-Dimethylaminoethoxyimino]methyl-5-(4-hydroxyphenyl)-7a-methylperhydroinden-3a-ol (I-ax)

¹H-NMR (300 MHz, DMSO-d₆, ppm from TMS): 0.88 (3H, s); 1.30–1.72 (8H, m); 2.02 (1H, m); 2.12 (6H, s); 2.25 (2H, m); 2.43 (2H, m); 2.52 (1H, m); 3.92 (2H, m); 4.30 (1H, s); 6.62 (2H, d); 7.00 (2H, d); 7.42 (1H, d); 9.10 (1H, s).

(1R,3aS,5S,7aR)-1-[(E,E)-2-Methyl-3-(2-aminoethoxyimino)]-1-propenyl]-5-(4-hydroxyphenyl)-7a-methylperhydroinden-3a-ol oxalate (I-ay)

¹H-NMR (300 MHz, CD₃OD, ppm from TMS): 0.86 (3H, s); 1.45–2.50 (10H, m); 1.84 (3H, s); 2.65 (1H, m); 2.78 (1H, m); 3.20 (2H, m); 4.18 (2H, m); 6.15 (1H, d); 6.78 (2H, d); 7.08 (2H, d); 7.67 (1H, s).

(1S,3aS,5S,7aR)-1-[(E)-2-Aminoethoxyimino]methyl-5-(3-hydroxymethylphenyl)-7a-methylperhydroinden-3a-ol oxalate (I-az)

¹H-NMR (300 MHz, CD₃OD, ppm from TMS): 1.00 (3H, s); 1.45–2.00 (8H, m); 2.15 (1H, m); 2.42 (2H, m); 2.72 (1H, m); 3.20 (2H, m); 4.18 (2H, m); 4.58 (2H, s); 7.10–7.30 (4H, m); 7.58 (1H, d).

(1S,3aS,5S,7aR)-1-[(E)-2-Dimethylaminoethoxyimino]methyl-5-(3-hydroxymethylphenyl)-7a-methylperhydroinden-3a-ol (I-ba)

¹H-NMR (300 MHz, DMSO-d₆, ppm from TMS): 0.89 (3H, s); 1.30–1.80 (8H, m); 2.05 (1H, m); 2.15 (6H, s); 2.28 (2H, m); 2.43 (2H, m); 2.68 (1H, m); 3.95 (2H, m); 4.31 (1H, s); 4.45 (2H, d); 5.12 (1H, t); 7.05–7.25 (4H, m); 7.48 (1H, d).

(1S,3aS,5S,7aR)-1-[(E)-2-Aminoethoxyimino]methyl-5-(4-hydroxymethylphenyl)-7a-methylperhydroinden-3a-ol (I-bb)

¹H-NMR (300 MHz, CDCl₃, ppm from TMS): 1.02 (3H, s); 1.40–2.00 (8H, m); 2.15 (1H, m); 2.37 (1H, m); 2.50 (1H, m); 2.72 (1H, m); 2.92 (2H, m); 4.05 (2H, m); 4.67 (2H, s); 7.22 (2H, dd); 7.31 (2H, dd); 7.63 (1H, d).

(1S,3aS,5S,7aR)-1-[(E)-2-Dimethylamino ethoxyimino]methyl-5-(4-hydroxymethylphenyl)-7a-methylperhydroinden-3a-ol (I-bc)

¹H-NMR (300 MHz, CDCl₃, ppm from TMS): 1.02 (3H, s); 1.40–2.00 (8H, m); 2.15 (1H, m); 2.28 (6H, s); 2.37 (1H, m); 2.50 (1H, m); 2.58 (2H, m); 2.72 (1H, m); 4.12 (2H, m); 4.67 (2H, s); 7.20 (2H, dd); 7.31 (2H, dd); 7.63 (1H, d).

(1S,3aS,5S,7aR)-1-[(E)-2-Aminoethoxyimino]methyl-5-(3-methylphenyl)-7a-methylperhydroinden-3a-ol oxalate (I-bd)

¹H-NMR (300 MHz, CD₃OD, ppm from TMS): 1.00 (3H, s); 1.47–1.90 (8H, m); 2.13 (1H, m); 2.29 (3H, s); 2.40 (2H, m); 2.69 (1H, m); 3.20 (2H, m); 4.18 (2H, m); 6.95–7.18 (4H, m); 7.63 (1H, d).

(1S,3aS,5S,7aR)-1-[(E)-2-Dimethylaminoethoxyimino]methyl-5-(3-methylphenyl)-7a-methylperhydroinden-3a-ol (I-be)

¹H-NMR (300 MHz, CD₃OD, ppm from TMS): 1.00 (3H, s); 1.47–1.90 (8H, m); 2.13 (1H, m); 2.28 (6H, s); 2.29 (3H, s); 2.40 (2H, m); 2.62 (2H, m); 2.69 (1H, m); 4.08 (2H, m); 6.95–7.18 (4H, m); 7.58 (1H, d).

(1R,3aS,5S,7aR)-1-[(E,E)-2-Methyl-3-(2-aminoethoxyimino)]-1-propenyl]-5-(3-methylphenyl)-7a-methylperhydroinden-3a-ol oxalate (I-bf)

¹H-NMR (300 MHz, CD₃OD, ppm from TMS): 0.85 (3H, s); 1.45–2.50 (13H, m); 1.84 (3H, s); 2.70 (2H, m); 3.20 (2H, m); 4.18 (2H, m); 6.12 (1H, d); 7.15 (4H, m); 7.67 (1H, s).

(1S,3aS,5S,7aR)-1-[(E)-2-Aminoethoxyimino]methyl-5-(4-methylphenyl)-7a-methylperhydroinden-3a-ol oxalate (I-bg)

¹H-NMR (300 MHz, CD₃OD, ppm from TMS): 1.05 (3H, s); 1.40–1.92 (8H, m); 2.13 (1H, m); 2.28 (3H, s); 2.45 (2H, m); 2.71 (1H, m); 3.21 (1H, m); 3.20 (2H, m); 4.15 (2H, m); 7.10 (4H, m); 7.63 (1H, d).

(1S,3aS,5S,7aR)-1-[(E)-2-Dimethylaminoethoxyimino]methyl-5-(4-methylphenyl)-7a-methylperhydroinden-3a-ol (I-bh)

¹H-NMR (300 MHz, CDCl₃, ppm from TMS): 1.05 (3H, s); 1.40–2.05 (8H, m); 2.12 (1H, m); 2.30 (6H, s); 2.31 (3H, s); 2.35 (1H, m); 2.49 (1H, m); 2.59 (2H, m); 2.69 (1H, m); 4.12 (2H, m); 7.10 (4H, m); 7.61 (1H, d).

(1R,3aS,5S,7aR)-1-[(E,E)-2-Methyl-3-(2-aminoethoxyimino)-1-propenyl]-5-(4-methylphenyl)-7a-methylperhydroinden-3a-ol oxalate (I-bi)

¹H-NMR (300 MHz, CD₃OD, ppm from TMS): 0.85 (3H, s); 1.45–2.50 (13H, m); 1.84 (3H, s); 2.70 (2H, m); 3.20 (2H, m); 4.18 (2H, m); 6.15 (1H, s); 7.15 (4H, m); 7.67 (1H, s).

(1S,3aS,5S,7aR)-1-[(E)-2-Dimethylaminoethoxyimino]methyl-5-[3-(2-dimethylaminoethoxy)phenyl]-7a-methylperhydroinden-3a-ol (I-bj)

¹H-NMR (300 MHz, CDCl₃, ppm from TMS): 1.03 (3H, s); 1.20–2.00 (8H, m); 2.15 (1H, m); 2.27 (6H, s); 2.33 (6H, s, and 1H, m); 2.50 (1H, m); 2.58 (2H, m); 2.69 (1H, m); 2.72 (2H, m); 4.03 (2H, m); 4.13 (2H, m); 6.80–7.20 (4H, m); 7.65 (1H, d).

(1S,3aS,5S,7aR)-1-[(E)-2-Aminoethoxyimino]methyl-5-[4-(2-dimethylaminoethoxy)phenyl]-7a-methylperhydroinden-3a-ol (I-bk)

¹H-NMR (300 MHz, CDCl₃, ppm from TMS): 1.03 (3H, s); 1.20–2.00 (8H, m); 2.15 (1H, m); 2.27 (6H, s); 2.33 (1H, m); 2.50 (1H, m); 2.58 (2H, m); 2.69 (1H, m); 2.80 (2H, m); 4.03 (2H, m); 4.13 (2H, m); 6.85 (2H, d); 7.13 (2H, d); 7.65 (1H, d).

(1S,3aS,5S,7aR)-1-[(E)-2-Dimethylaminoethoxyimino]methyl-5-4-(2-dimethylaminoethoxyphenyl]-7a-methylperhydroinden-3a-ol (I-bl)

¹H-NMR (300 MHz, CDCl₃, ppm from TMS): 1.03 (3H, s); 1.20–2.00 (8H, m); 2.15 (1H, m); 2.27 (6H, s); 2.33 (6H, s, and 1H, m); 2.50 (1H, m); 2.58 (2H, m); 2.65 (1H, m) 2.72 (2H, m); 4.03 (2H, m); 4.13 (2H, m); 6.85 (2H, d); 7.13 (2H, d); 7.65 (1H, d).

(1S,3aS,5S,7aR)-1-[(E)-2-Dimethylaminoethoxyimino]methyl-5-(2-hydroxyethoxy)-7a-methylperhydroinden-3a-ol oxalate (I-bm)

¹H-NMR (300 MHz, CD₃OD, ppm from TMS): 1.03 (3H, s); 1.40–2.50 (11H, m); 2.95 (6H, s); 3.24 (2H, m); 3.50–3.71 (4H, m); 3.75 (1H, m); 4.13 (2H, m); 7.55 (1H, d).

(1S,3aS,5S,7aR)-1-[(E)-2-Aminoethoxyimino]methyl-5-[2-(2-dimethylaminoethoxy)ethoxy]-7a-methylperhydroinden-3a-ol oxalate (I-bn)

¹H-NMR (300 MHz, CD₃OD, ppm from TMS): 1.03 (3H, s); 1.40–2.50 (11H, m); 2.90 (6H, s); 3.24 (2H, m); 3.40 (2H, m); 3.50–3.75 (5H, m); 4.15 (4H, m); 7.55 (1H, d).

(1S,3aS,5R,7aR)-1-[(E)-2-Aminoethoxyimino]methyl-5-(3-hydroxypropyl)-7a-methylperhydroinden-3a-ol oxalate (I-bo)

¹H-NMR (300 MHz, CD₃OD, ppm from TMS): 1.03 (3H, s); 1.30–2.50 (16H, m); 3.23 (2H, m); 3.65–3.72 (2H, m); 4.18 (2H, m); 7.50 (1H, d).

(1S,3aS,5R,7aR)-1-[(E)-2-Aminoethoxyimino]methyl-5-(3-dimethylaminopropyl)-7a-methylperhydroinden-3a-ol oxalate (I-bp)

¹H-NMR (300 MHz, CD₃OD, ppm from TMS): 1.03 (3H, s); 1.30–2.50 (16H, m); 2.95 (6H, s); 3.23 (2H, m); 3.39 (2H, m); 4.18 (2H, m); 7.59 (1H, d).

(1S,3aS,5S,7aR)-1-[(E)-2-Aminoethoxyimino]methyl-5-(4-hydroxybutyl)-7a-methylperhydroinden-3a-ol oxalate (I-bq)

¹H-NMR (300 MHz, CD₃OD, ppm from TMS): 1.03 (3H, s); 1.30–2.50 (18H, m); 3.23 (2H, m); 3.65–3.72 (2H, m); 4.18 (2H, m); 7.50 (1H, d).

(1S,3aS,5S,7aR)-1-[(E)-2-Aminoethoxyimino]methyl-5-(4-dimethylaminobutyl)-7a-methylperhydroinden-3a-ol oxalate (I-br)

¹H-NMR (300 MHz, CD₃OD, ppm from TMS): 1.03 (3H, s); 1.30–2.50 (18H, m); 2.95 (6H, s); 3.23 (2H, m); 3.39 (2H, m); 4.18 (2H, m); 7.59 (1H, d).

(1S,3aS,5R,7aR)-1-[(E)-2-Amino ethoxyimino]methyl-5-benzyl-7a-methylperhydroinden-3a-ol (I-bs)

¹H-NMR (300 MHz, DMSO-d₆, ppm from TMS): 0.80 (3H, s); 1.10–1.70 (9H, m); 1.96 (2H, m); 2.18 (1H, m); 2.43 (2H, m); 2.50 (2H, s); 3.91 (2H, m); 4.20 (1H, s); 7.10–7.28 (5H, m); 7.41 (1H, d).

(1S,3aS,5R,7aR)-1-[(E)-2-Dimethylaminoethoxyimino]methyl-5-benzyl-7a-methylperhydroinden-3a-ol (I-bt)

¹H-NMR (300 MHz, DMSO-d₆, ppm from TMS): 0.80 (3H, s); 1.10–1.70 (9H, m); 1.96 (2H, m); 2.10 (6H, s); 2.18 (1H, m); 2.43 (2H, m); 2.50 (2H, s); 3.91 (2H, m); 4.20 (1H, s); 7.10–7.28 (5H, m); 7.41 (1H, d).

(1S,3aS,5R,7aR)-1-[(E)-2-Aminoethoxyimino]methyl-5-(4-hydroxybenzyl)-7a-methylperhydroinden-3a-ol oxalate (I-bu)

¹H-NMR (300 MHz, CD₃OD, ppm from TMS): 1.00 (3H, s); 1.40–2.50 (14H, m); 3.20 (2H, m); 4.18 (2H, m); 6.75 (2H, d); 7.10 (2H, d); 7.65 (1H, d).

(1S,3aS,5R,7aR)-1-[(E)-2-Dimethylaminoethoxyimino]methyl-5-(4-hydroxybenzyl)-7a-methylperhydroinden-3a-ol oxalate (I-bv)

¹H-NMR (300 MHz, CD₃OD, ppm from TMS): 1.00 (3H, s); 1.40–2.50 (14H, m); 2.92 (6H, s); 3.42 (2H, m); 4.18 (2H, m); 6.75 (2H, d); 7.10 (2H, d); 7.65 (1H, d).

(1S,3aS,5R,7aR)-1-[(E)-2-Aminoethoxyimino]methyl-5-(4-hydroxymethylbenzyl)-7a-methylperhydroinden-3a-ol oxalate (I-bw)

¹H-NMR (300 MHz, CDCl₃, ppm from TMS): 1.02 (3H, s); 1.40–2.50 (14H, m); 3.20 (2H, m); 4.18 (2H, m); 4.67 (2H, s); 7.20 (2H, d); 7.31 (2H, d); 7.65 (1H, d).

(1S,3aS,7aR)-1-[(E)-2-Dimethylaminoethoxyimino]methyl-5-[(Z)-3-hydroxypropyliden]-7a-methylperhydroinden-3a-ol (I-bx)

¹H-NMR (300 MHz, CD₃OD, ppm from TMS): 0.95 (3H, s); 1.40–2.55 (13H, m); 2.28 (6H, s); 2.62 (2H, m); 3.52 (2H, m); 4.10 (2H, m); 5.25 (1H, m); 7.50 (1H, d).

(1S,3aS,7aR)-1-[(E)-2-Dimethylaminoethoxyimino]methyl-5-[(E)-3-hydroxypropyliden]-7a-methylperhydroinden-3a-ol (I-by)

¹H-NMR (300 MHz, CD₃OD, ppm from TMS): 0.92 (3H, s); 1.30–2.25 (13H, m); 2.32 (6H, s); 2.67 (2H, m); 3.52 (2H, m); 4.12 (2H m); 5.15 (1H, m); 7.51 (1H, d).

(1S,3aS,7aR)-1-[(E)-2-Dimethylaminoethoxyimino]methyl-5-[(Z)-3-(2-dimethylaminoethoxy)propyliden]-7a-methylperhydroinden-3a-ol oxalate (I-bz)

¹H-NMR (300 MHz, CD₃OD, ppm from TMS): 0.95 (3H, s); 1.40–2.55 (13H, m); 2.28 (6H, s); 2.31 (6H, s); 2.65 (4H, m); 3.50 (2H, m); 4.18 (2H, m); 5.25 (1H, m); 7.50 (1H, d).

(1S,3aS,7aR)-1-[(E)-2-Dimethylaminoethoxyimino]methyl-5-[(Z)-3-dimethylaminopropyliden]-7a-methylperhydroinden-3a-ol oxalate (I-ca)

¹H-NMR (300 MHz, CD₃OD, ppm from TMS): 0.98 (3H, s); 1.40–2.50 (13H, m); 2.93 (6H, s); 2.95 (6H, s); 3.45 (4H, m); 4.18 (2H, m); 5.18 (1H, m); 7.50 (1H, d).

(1S,3aS,7aR)-1-[(E)-2-Dimethylaminoethoxyimino]methyl-5-[(E)-3-dimethylaminopropyliden]-7a-methylperhydroinden-3a-ol oxalate (I-cb)

¹H-NMR (300 MHz, CD₃OD, ppm from TMS): 0.92 (3H, s); 1.30–2.25 (13H, m); 2.93 (6H, s); 2.95 (6H, s); 3.38 (4H, m); 4.18 (2H, m); 5.11 (1H, m): 7.50 (1H, d).

(1S,3aS,5S,7aR)-1-[(E)-2-Aminoethoxyimino]methyl-5-[(E)-4-hydroxy-1-butenyl]-7a-methylperhydroinden-3a-ol oxalate (I-cc)

¹H-NMR (300 MHz, CD₃OD, ppm from TMS): 1.10 (3H, s); 1.40–2.52 (14H, m); 3.30 (2H, m); 3.71 (2H, m); 4.18 (2H, m); 5.30 (1H, dd); 5.55 (1H, dd); 7.65 (1H, d).

(1S,3aS,5S,7aR)-1-[(E)-2-Dimethylamino ethoxyimino]methyl-5-(E)-4-hydroxy-1-butenyl]-7a-methylperhydroinden-3a-ol oxalate (I-cd)

¹H-NMR (300 MHz, CD₃OD, ppm from TMS): 1.10 (3H, s); 1.40–2.52 (14H, m); 2.95 (6H, s); 3.43 (2H, m); 3.71 (2H, m); 4.18 (2H, m); 5.30 (1H, dd); 5.55 (1H, dd); 7.65 (1H, d).

(1S,3aS,5S,7aR)-1-[(E)-2-Aminoethoxyimino]methyl-5-[(E)-4-dimethylamino-1-butenyl]-7a-methylperhydroinden-3a-ol oxalate (I-ce)

¹H-NMR (300 MHz, CD₃OD, ppm from TMS): 1.00 (3H, s); 1.40–2.50 (14H, m); 2.92 (6H, s); 3.43 (4H, m); 4.18 (2H, m); 5.30 (1H, dd); 5.55 (1H, dd); 7.65 (1H, d).

(1S,3aS,7aR)-1-[(E)-2-Dimethylamino ethoxyimino]methyl-5-[(Z)-benzyliden]-7a-methylperhydroinden-3a-ol (I-cf)

¹H-NMR (300 MHz, CDCl₃, ppm from TMS): 1.02 (3H, s); 1.51–2.11 (7H, m); 2.27 (6H, s); 2.38 (2H, m); 2.61 (2H, m); 2.71 (2H, m); 4.12 (2H, m); 6.41 (1H, m); 7.18–7.35 (5H, m); 7.52 (1H, d).

(1S,3aS,7aR)-1-[(E)-2-Dimethylaminoethoxyimino]methyl-5-[(E)-benzyliden]-7a-methylperhydroinden-3a-ol (I-cg)

$^1$H-NMR (300 MHz, CDCl$_3$, ppm from TMS): 0.90 (3H, s); 1.35–2.10 (6H, m); 2.30 (2H, m); 2.31 (6H, s); 2.40 (1H, m); 2.51 (1H, m); 2.57 (2H, m); 2.71 (1H, m); 4.12 (2H, m); 6.28 (1H, m) 7.12–7.31 (5H, m); 7.51 (1H, d).

(1S,3aS,5S,7aR)-1-[(E)-2-Aminoethoxyimino]methyl-5-cyclohexyl-7a-methylperhydroinden-3a-ol oxalate (I-ch)

$^1$H-NMR (300 MHz, DMSO-d$_6$, ppm from TMS): 0.78 (3H, s); 0.80–1.71 (20H, m); 2.01 (2H, m); 2.22 (1H, m); 2.92 (2H, m); 3.98 (2H, m); 7.51 (1H, d).

(1S,3aS,5S,7aR)-1-[(E)-3-Aminopropoxyimino]methyl-5-cyclohexyl-7a-methylperhydroinden-3a-ol oxalate (I-ci)

$^1$H-NMR (300 MHz, CDCl$_3$, ppm from TMS): 0.90 (3H, s); 0.91–1.80 (22H, m); 2.15 (2H, m); 2.41 (1H, m); 2.80 (2H, m); 4.08 (2H, m); 7.55 (1H, d).

(1S,3aS,5S,7aR)-1-[(E)-4-Aminobutoxyimino]methyl-5-cyclohexyl-7a-methylperhydroinden-3a-ol oxalate (I-cj)

$^1$H-NMR (300 MHz, CD$_3$OD, ppm from TMS): 0.90 (3H, s); 0.80–1.80 (24H, m); 2.15 (2H, m); 2.43 (1H, m); 3.28 (2H, m); 4.10 (2H, m); 7.65 (1H, d).

(1S,3aS,5S,7aR)-1-[(E)-2-Dimethylaminoethoxyimino]methyl-5-cyclohexyl-7a-methylperhydroinden-3a-ol (I-ck)

$^1$H-NMR (300 MHz, CD$_3$OD, ppm from TMS): 0.89 (3H, s); 0.95–1.80 (20H, m); 2.09 (1H, m); 2.21 (1H, m); 2.26 (6H, s); 2.35 (1H, m); 2.61 (2H, m); 4.05 (2H, m); 7.52 (1H, d).

(1S,3aS,5S,7aR)-1-[(E)-3-Dimethylaminopropoxyimino]methyl-5-cyclohexyl-7a-methylperhydroinden-3a-ol oxalate (I-cl)

$^1$H-NMR (300 MHz, CD$_3$OD, ppm from TMS): 0.89 (3H, s); 0.95–1.80 (20H, m); 2.09 (3H, m); 2.21 (1H, m); 2.43 (1H, m); 2.88 (6H, s); 3.20 (2H, m); 4.05 (2H, m); 7.55 (1H, d).

(1S,3aS,5S,7aR)-1-[(E)-4-Dimethylaminobutoxyimino]methyl-5-cyclohexyl-7a-methylperhydroinden-3a-ol (I-cm)

$^1$H-NMR (300 MHz, CDCl$_3$, ppm from TMS): 0.90 (3H, s); 0.91–2.20 (24H, m); 2.22 (6H, s); 2.27 (2H, m); 2.41 (1H, m); 4.00 (2H, m); 7.55 (1H, d).

(1R,3aS,5S,7aR)-1-[(E,E)-3-(2-Aminoethoxyimino)-1-propenyl]-5-cyclohexyl-7a-methylperhydroinden-3a-ol oxalate (I-cn)

$^1$H-NMR (300 MHz, DMSO-d$_6$, ppm from TMS): 0.71 (3H, s); 0.82–1.72 (20H, m); 2.00 (2H, m); 2.21 (1H, m); 3.02 (2H, m); 4.08 (2H, m); 5.85 (1H, dd); 6.31 (1H, dd); 7.80 (1H, d).

(1R,3aS,5S,7aR)-1-[(E,E)-3-(2-Dimethylaminoethoxyimino)-1-propenyl]-5-cyclohexyl-7a-methylperhydroinden-3a-ol oxalate (I-co)

$^1$H-NMR (300 MHz, DMSO-d$_6$, ppm from TMS): 0.71 (3H, s); 0.81–1.75 (20H, m); 2.00 (2H, m); 2.21 (1H, m); 2.68 (6H, s); 3.18 (2H, m); 4.17 (2H, m); 5.85 (1H, dd); 6.31 (1H, dd); 7.80 (1H, d).

(1R,3aS,5S,7aR)-1-[(E,E)-2-Methyl-3-(2-aminoethoxyimino)]-1-propenyl]-5-cyclohexyl-7a-methylperhydroinden-3a-ol oxalate (I-cp)

$^1$H-NMR (300 MHz, CD$_3$OD, ppm from TMS): 0.85 (3H, s); 0.90–1.65 (20H, m); 1.83 (3H, s); 2.05–2.40 (2H, m); 2.80 (1H, m); 3.20 (2H, m); 4.18 (2H, m); 6.15 (1H, d); 7.67 (1H, s).

(1R,3aS,5S,7aR)-1-[(E,E)-2-Methyl-3-(2-dimethylaminoethoxyimino)-1-propenyl]-5-cyclohexyl-7a-methylperhydroinden-3a-ol oxalate (I-cq)

$^1$H-NMR (300 MHz, CD$_3$OD, ppm from TMS): 0.85 (3H, s); 0.90–1.65 (20H, m); 1.83 (3H, s); 2.05–2.40 (2H, m); 2.80 (1H, m); 2.90 (6H, s); 3.43 (2H, m); 4.35 (2H, m); 6.15 (1H, d); 7.65 (1H, s).

(1S,3aS,5R,7aR)-1-[(E)-2-Aminoethoxyimino]methyl-5-cyclohexylmethyl-7a-methylperhydroinden-3a-ol (I-cr)

$^1$H-NMR (300 MHz, CD$_3$OD, ppm from TMS): 0.88 (3H, s, and 1H, m); 1.03–1.78 (21H, m); 2.08 (1H, m); 2.20 (1H, m); 2.35 (1H, m); 2.62 (2H, m); 4.01 (2H, m); 7.59 (1H, d).

(1S,3aS,5R,7aR)-1-[(E)-2-Dimethylamino ethoxyimino]methyl-5-cyclohexylmethyl-7a-methylperhydroinden-3a-ol (I-cs)

$^1$H-NMR (300 MHz, CD$_3$OD, ppm from TMS): 0.88 (3H, s and 1H, m); 1.02–1.78 (21H, m); 2.08 (1H, m); 2.20 (1H, m); 2.29 (6H, s); 2.35 (1H, m); 2.62 (2H, m); 4.08 (2H, m); 7.52 (1H, d).

(1S,3aS,5S,7aR)-1-[(E)-2-Aminoethoxyimino]methyl-5-(3-pyridyl)-7a-methylperhydroinden-3a-ol (I-ct)

$^1$H-NMR (300 MHz, CDCl$_3$, ppm from TMS): 1.03 (3H, s); 1.48–2.21 (9H, m); 2.37 (1H, m); 2.52 (1H, m); 2.59 (2H, m); 2.73 (1H, m); 4.11 (2H, m); 7.22 (1H, m); 7.52 (1H, m); 7.62 (1H, d); 8.45 (2H, m).

(1S,3aS,5S,7aR)-1-[(E)-2-Dimethylaminoethoxyimino]methyl-5-(3-pyridyl)-7a-methylperhydroinden-3a-ol (I-cu)

$^1$H-NMR (300 MHz, CDCl$_3$, ppm from TMS): 1.02 (3H, s); 1.48–2.21 (9H, m); 2.28 (6H, s); 2.36 (1H, m); 2.52 (1H, m); 2.58 (2H, m); 2.73 (1H, m); 4.11 (2H, m); 7.22 (1H, m); 7.52 (1H, m); 7.62 (1H, d); 8.45 (2H, m).

(1S,3aS,5S,7aR)-1-[(E)-2-Aminoethoxyimino]methyl-5-(4-pyridyl)-7a-methylperhydroinden-3a-ol (I-cv)

$^1$H-NMR (300 MHz, CDCl$_3$, ppm from TMS): 1.03 (3H, s); 1.48–2.21 (9H, m); 2.37 (1H, m); 2.52 (1H, m); 2.59 (2H, m); 2.65 (1H, m); 4.11 (2H, m); 7.15 (2H, d); 7.62 (1H, d); 8.35 (2H, d).

(1S,3aS,5S,7aR)-1-[(E)-2-Dimethylaminoethoxyimino]methyl-5-(4-pyridyl)-7a-methylperhydroinden-3a-ol (I-cw)

$^1$H-NMR (300 MHz, CDCl$_3$, ppm from TMS): 1.02 (3H, s); 1.48–2.21 (9H, m); 2.28 (6H, s); 2.36 (1H, m); 2.52 (1H, m); 2.58 (2H, m); 2.65 (1H, m); 4.11 (2H, m); 7.15 (2H, d); 7.62 (1H, d); 8.35 (2H, m).

(1S,3aS,5S,7aR)-1-[(E)-2-Amino ethoxyimino]methyl-5-(4-cis-hydroxy-r-1-cyclohexyl)-7a-methylperhydroinden-3a-ol (I-cx)

$^1$H-NMR (300 MHz, CD$_3$OD, ppm from TMS): 0.88 (3H, s); 1.01–1.98 (18H, m); 2.08 (1H, m); 2.21 (1H, m); 2.35 (1H, m); 2.61 (2H, m); 3.88 (1H, m); 4.08 (2H, m); 7.53 (1H, d).

(1S,3aS,5S,7aR)-1-[(E)-2-Dimethylaminoethoxyimino]methyl-5-(4-cis-hydroxy-r-1-cyclohexyl)-7a-methylperhydroinden-3a-ol (I-cy)

$^1$H-NMR (300 MHz, CD$_3$OD, ppm from TMS): 0.88 (3H, s); 1.01–1.98 (18H, m); 2.08 (1H, m); 2.21 (1H, m); 2.28 (6H, s); 2.35 (1H, m); 2.61 (2H, m); 3.88 (1H, m); 4.08 (2H, m); 7.53 (1H, d).

(1S,3aS,5S,7aR)-1-[(E)-2-Aminoethoxyimino]methyl-5-(4-trans-hydroxy-r-1-cyclohexyl)-7a-methylperhydroinden-3a-ol (I-cz)

$^1$H-NMR (300 MHz, CD$_3$OD, ppm from TMS): 0.88 (3H, s); 1.01–1.98 (18H, m); 2.08 (1H, m); 2.21 (1H, m); 2.35 (1H, m); 2.61 (2H, m); 3.52 (1H, m); 4.08 (2H, m); 7.53 (1H, d).

(1S,3aS,5S,7aR)-1-[(E)-2-Dimethylaminoethoxyimino]methyl-5-(4-trans-hydroxy-r-1-cyclohexyl)-7a-methylperhydroinden-3a-ol (I-da)

¹H-NMR (300 MHz, CD₃OD, ppm from TMS): 0.88 (3H, s); 1.01–1.98 (18H, m); 2.08 (1H, m); 2.21 (1H, m); 2.28 (6H, s); 2.35 (1H, m); 2.61 (2H, m); 3.52 (1H, m); 4.08 (2H, m); 7.53 (1H, d).

EXAMPLE 5

(1S,3aS,5S,7aR)-1-[(E)-2-Guanidinoethoxyimino]methyl-5-phenyl-7a-methylperhydroinden-3a-ol nitrate (I-db)

A solution of 0.75 g of (1S,3aS,5S,7aR)-1-[(E)-2-aminoethoxyimino]methyl-5-phenyl-7a-methylperhydroinden-3a-ol (I-am) and 1.05 g of 1-amidino-3,5-dimethylpirazole nitrate in 20 ml of ethanol was heated at reflux for 10 hrs. The solution was evaporated to dryness under reduced pressure and the residue was purified by flash chromatography (SiO₂) with chloroform/methanol/28% ammonium hydroxide 78:20:2 as the eluant. The fractions containing the title compound were collected and evaporated to dryness. The residue was ground with diisopropyl ether:ethanol 9:1 to give 0.42 g of the title compound (I-db) as a white solid.

¹H-NMR (300 MHz, CD₃OD, ppm from TMS): 1.00 (3H, s); 1.45–2.55 (11H, m); 2.73 (1H, m); 3.23 (2H, m); 4.10 (2H, m); 7.10–7.30 (5H, m); 7.58 (1H, d).

EXAMPLE 6

(1S,3aS,5S,7aR)-1-Guanidinoaminomethyl-5-phenyl-7a-methylperhydroinden-3a-ol oxalate (I-dc)

A solution of 0.45 g of (1S,3aS,5S,7aR)-1-[(E)-guanidinoimino]methyl-5-phenyl-7a-methylperhydroinden-3a-ol (I-aa) in 6 ml of methanol was made acid to pH 3 with 1N HCl. To this solution 0.30 g of NaBH₃CN were added while maintaining the pH in 2.8+3.0 range with 0.1N HCl. After 6 hrs 0.15 g of NaBH₃CN were added and the mixture was stirred overnight. The mixture was alkalinized to pH 10 with 2.5N NaOH, concentrated under reduced pressure and extracted with ethyl acetate. The organic layer was dried over anhydrous sodium sulfate and evaporated to dryness. The residue was purified by flash-chromatography (SiO₂) with chloroform/methanol/28% ammonium hydroxide 78:20:2 as the eluant. The fractions containing the title compound were collected and evaporated to dryness. The residue was dissolved in ethyl acetate and reacted with the stoichiometric amount of oxalic acid to give 0.43 g of the title compound (I-dc) as a white solid.

¹H-NMR (300 MHz, CD₃OD, ppm from TMS): 1.00 (3H, s); 1.45–2.55 (11H, m); 2.75 (1H, m); 2.93 (1H, m); 3.15 (1H, m); 7.10–7.30 (5H, m).

Using the same procedure described in Ex. 6 and starting from the appropriate imino derivatives, the following compounds were obtained:

(1S,3aS,5S,7aR)-1-(2-Aminoethoxyamino)methyl-5-phenyl-7a-methylperhydroinden-3a-ol oxalate (I-dd)

¹H-NMR (300 MHz, CD₃OD, ppm from TMS): 1.00 (3H, s); 1.50–1.90 (9H, m); 2.01 (1H, m); 2.32 (1H, m); 2.73 (1H, m); 2.93 (1H, m); 3.15 (3H, m); 3.88 (2H, m); 7.12–7.30 (5H, m).

(1S,3aS,5S,7aR)-1-(3-Aminopropoxyamino)methyl-5-phenyl-7a-methylperhydroinden-3a-ol oxalate (I-de)

¹H-NMR (300 MHz, CDCl₃, ppm from TMS): 1.08 (3H, s); 1.50–2.10 (12H, m); 2.32 (1H, m); 2.75 (1H, m); 2.90 (1H, m); 3.20 (3H, m); 3.88 (2H, m); 7.10–7.30 (5H, m).

(1S,3aS,5S,7aR)-1-(2-Dimethylaminoethoxyamino)methyl-5-phenyl-7a-methylperhydroinden-3a-ol oxalate (I-df)

¹H-NMR (300 MHz, CD₃OD, ppm from TMS): 1.08 (3H, s); 1.50–1.90 (10H, m); 2.35 (1H, m); 2.72 (1H, m); 2.92 (6H, s); 2.98 (1H, dd); 3.20 (1H, dd); 3.37 (2H, m); 3.98 (2H, m); 7.10–7.30 (5H, m).

(1S,3aS,5S,7aR)-1-(3-Dimethylaminopropoxyamino)methyl-5-phenyl-7a-methylperhydroinden-3a-ol oxalate (I-dg)

¹H-NMR (300 MHz, CD₃OD, ppm from TMS): 1.00 (3H, s); 1.40–2.50 (13H, m); 2.73 (1H, m); 2.95 (6H, s); 2.98 (1H, dd); 3.18 (1H, dd); 3.38 (2H, m); 4.02 (2H, m); 7.10–7.30 (5H, m).

(1R,3aS,5S,7aR)-1-[(E)-2-Methyl-3-(2-dimethylaminoethoxyamino)-1-propenyl]-5-phenyl-7a-methylperhydroinden-3a-ol oxalate (I-dh)

¹H-NMR (300 MHz, CD₃OD, ppm from TMS): 0.85 (3H, s); 1.45–2.50 (10H, m); 1.74 (3H, s); 2.73 (2H, m); 2.95 (6H, s); 3.23 (2H, m); 3.43 (2H, m); 4.17 (2H, m); 5.55 (1H, m); 7.10–7.30 (5H, m).

(1S,3aS,5S,7aR)-1-(2-Dimethylaminoethoxyamino)methyl-5-(3-hydroxyphenyl)-7a-methylperhydroinden-3a-ol oxalate (I-di)

¹H-NMR (300 MHz, CD₃OD, ppm from TMS): 1.05 (3H, s); 1.45–2.50 (11H, m); 2.65 (1H, m); 2.90 (6H, s); 2.98 (1H, dd); 3.20 (1H, dd); 3.37 (2H, m); 3.98 (2H, m); 6.68–7.15 (4H, m).

(1S,3aS,5S,7aR)-1-(2-Aminoethoxyamino)methyl-5-(4-hydroxyphenyl)-7a-methylperhydroinden-3a-ol oxalate (I-dj)

¹H-NMR (300 MHz, CD₃OD, ppm from TMS): 1.05 (3H, s); 1.45–2.35 (11H, m); 2.65 (1H, m); 2.93 (1H, m); 3.13 (3H, m); 3.88 (2H, m); 6.78 (2H, d); 7.08 (2H d).

(1S,3aS,5S,7aR)-1-(2-Dimethylaminoethoxyamino]methyl-5-(4-hydroxymethylphenyl)-7a-methylperhydroinden-3a-ol oxalate (I-dk)

¹H-NMR (300 MHz, CDCl₃, ppm from TMS): 1.05 (3H, s); 1.40–2.55 (11H, m); 2.71 (1H, m); 2.90 (6H, s); 2.95 (1H, dd); 3.05 (1H, dd); 3.43 (2H, m); 4.18 (2H, m); 4.70 (2H, s); 7.20 (2H, dd); 7.31 (2H, dd).

(1S,3aS,5R,7aR)-1-(2-Aminoethoxyamino)methyl-5-benzyl-7a-methylperhydroinden-3a-ol oxalate (I-dl)

¹H-NMR (300 MHz, CD₃OD, ppm from TMS): 1.00 (3H, s); 1.40–2.50 (14H, m); 2.95 (1H, dd); 3.10 (1H, dd); 3.20 (2H, m); 4.18 (2H, m); 7.18–7.38 (5H, m).

(1R,3aS,5S,7aR)-1-[(E)-3-(2-Aminoethoxyamino)]-1-propenyl]-5-phenyl-7a-methylperhydroinden-3a-ol oxalate (I-dm)

The title compound (I-dm) (0.61 g) was obtained as an oxalate, white solid, starting from (1R,3aS,5S,7aR)-[(E)-2-formyl-1-ethenyl]-5-phenyl-7a-methyl-perhydroinden-3a-ol and 2-aminoethoxyamine, using the same procedure described in Ex. 4, and reacting the crude product with NaBH₃CN, using the same procedure described in Ex. 6.

¹H-NMR (300 MHz, CDCl₃, ppm from TMS): 0.80 (3H, s); 1.45–2.50 (11H, m); 2.73 (1H, m); 3.23 (4H, m); 4.15 (2H, m); 5.30 (1H, dt); 5.55 (1H, dd); 7.10–7.30 (5H, m).

PREPARATION 1

(1S,3aS,5S,7aR)-1-Form -5-(3-hydroxymethylphenyl)-7a-methylperhydroinden-3a-ol (II-aa)

A solution of 40.0 g of (3aS,7aS)-3a-hydroxy-7a-methyl-1,5-perhydroindendione (Hajos Z. G. and Parrish D. R., *J. Org. Chem.*, 1974, 39, 1615), 12.0 g of oxalic acid and 440 ml of ethylene glycol in 600 ml of acetonitrile was stirred at room temperature for 24 hrs. The mixture was made alkaline with 5% aqueous NaHCO₃, concentrated under reduced pressure and extracted with chloroform; the organic layer was dried over sodium sulfate and evaporated to dryness under reduced pressure to give 47.0 g of (3aS,7aS)-3a-hydroxy-5-spiro-2'-(1',3'-dioxolane)-7a-methyl-1-perhydroindenone as a dense yellowish off that was used without further purification.

$^1$H-NMR (300 MHz, CDCl$_3$, ppm from TMS): 0.99 (3H, s); 1.30–2.60 (10H, m); 3.96 (4H, m).

To a solution of 47.0 g of (3aS,7aS)-3a-hydroxy-5-spiro-2'-(1',3'-dioxolane)-7a-methyl-1-perhydroindenone and 790.0 g of methyltriphenylphosphonium bromide in 500 ml of anhydrous THF and 100 ml of DMSO, 248.0 g of potassium tert-butoxide were added, followed by the dropwise addition of 20 ml of tert-butanol. The mixture was heated at reflux for 2 hrs then cooled, neutralised with 5% aqueous Na$_2$HPO$_4$.12H$_2$O and extracted with ethyl acetate. The organic layer was washed with water, dried over sodium sulfate and evaporated to dryness under reduced pressure. The residue was purified by flash-chromatography (SiO$_2$) with methylene chloride/ethyl acetate 97:3 followed by 95:5 as the eluant to give 44.0 g of (3aS,7aR)-1-methylen-5-spiro-2'-(1',3'-dioxolane)-7a-methylperhydroinden-3a-ol as a colourless off.

$^1$H-NMR (300 MHz, CDCl$_3$, ppm from TMS): 0.98 (3H, s); 1.45–2.60 (10H, m); 3.40 (1H, bs); 3.95 (4H, m); 4.80 (2H, dt).

To a solution of 97.0 ml of BH$_3$.THF in 400 ml of anhydrous THF, 20.0 g of (3aS,7aR)-1-methylen-5-spiro-2'-(1',3'-dioxolane)-7a-methylperhydroinden-3a-ol in 40 ml of anhydrous THF were added and the mixture was stirred for 3 hrs at room temperature under a nitrogen atmosphere. The solution was cooled to 0° C. and water (50 ml), NaBO$_3$.H$_2$O (7.80 g) and 4N NaOH (13 ml) were successively added and the mixture was stirred at room temperature overnight. The mixture was neutralised with 5% aqueous NaH$_2$PO$_4$.H$_2$O and extracted with ethyl acetate; the organic layer was washed with water, dried over sodium sulfate and evaporated to dryness under reduced pressure. The residue was purified by flash-chromatography (SiO$_2$) with n-hexane/acetone/chloroform 4:3:3 as the eluant to give 10.6 g of (1S,3aS,7aR)-1-hydroxymethyl-5-spiro-2'-(1',3'-dioxolane)-7a-methylperhydroinden-3a-ol as a white foam.

$^1$H-NMR (300 MHz, CDCl$_3$, ppm from TMS): 0.89 (3H, s); 1.42–1.95 (11H, m); 3.59 (1H, dd); 3.60 (1H, dd); 3.98 (4H, m).

8.00 g of (1S,3aS,7aR)-1-hydroxymethyl-5-spiro-2'-(1',3'-dioxolane)-7a-methylperhydroinden-3a-ol were dissolved in 80 ml of 1N PTSA in acetonitrile/water 85:15 and the solution was stirred at room temperature for 24 hrs. The mixture was made alkaline with 5% aqueous NaHCO3, concentrated under reduced pressure and extracted with ethyl acetate. The organic layer was dried over sodium sulfate and evaporated to dryness under reduced pressure to give 4.95 g of (1S,3aS,7aR)-1-hydroxymethyl-3a-hydroxy-7a-methyl-5-perhydroindenone.

$^1$H-NMR (300 MHz, CDCl$_3$, ppm from TMS): 1.21 (3H, s); 1.55–1.98 (5H, m); 2.18–2.28 (2H, m); 2.40–2.65 (4H, m); 3.08 (1H, bs); 3.61 (1H, dd); 3.82 (1H, dd); 4.32 (1H, bs).

To a suspension of 60.0 g of 3-(tert-butyldimethylsilyloxymethyl)bromobenzene (prepared from tert-butyldimethylchlorosilane and 3-bromobenzyl alcohol according to the procedure described by Kendall P. M. et al., *J. Org. Chem.*, 1979, 44, 1421) in 500 ml of anhydrous THF cooled to −78° C., 131 ml of 1.6M n-butyllithium in n-hexane were added under a nitrogen atmosphere and the resulting mixture was stirred for 2.5 hrs. A solution of 6.30 g of (1S,3aS,7aR)-1-hydroxymethyl-3a-hydroxy-7a-methyl-5-perhydroindenone in 60 ml of anhydrous THF was added. After 1 hr the reaction mixture was allowed to warm to 0° C., and cautiously quenched with 300 ml of 5% aqueous NaH$_2$PO$_4$.H$_2$O and extracted with ethyl acetate. The organic layer was dried over sodium sulfate and evaporated to dryness under reduced pressure. The residue was purified by flash-chromatography (SiO$_2$) with n-hexane/acetone/chloroform 6:2:2 as the eluant to give 9.62 g of (1S,3aS,5R,7aR)-1-hydroxymethyl-5-(3-tert-butyldimethylsilyloxymethylphenyl)-7a-methylperhydroinden-3a,5-diol as a white foam.

$^1$H-NMR (300 MHz, CDCl$_3$, ppm from TMS): 0.09 (6H, s); 0.98 (9H, s); 1.12 (3H, s); 1.38 (1H, m); 1.55–2.15 (9H, m); 2.88 (1H, m); 3.45 (1H, bs); 3.51 (1H, dd); 3.78 (1H, dd); 4.72 (2H, s); 7.20–7.48 (4H m).

9.50 g of (1S,3aS,5R,7aR)-1-hydroxymethyl-5-(3-tert-butyldimethylsilyloxymethylphenyl)-7a-methylperhydroinden-3a,5-diol were first reacted with acetic anhydride in dry pyridine and then with 3N HCl in dioxane (pH 1), at room temperature for 1 hr to give 6.75 g of (1S,3aS,5R,7aR)-1-acetoxymethyl-5-(3-hydroxymethylphenyl)-7a-methylperhydroinden-3a,5-diol, as a white foam, that was dissolved in 15 ml of ethanol and reacted with 7.00 g of Raney-nickel (50% slurry in water) at reflux temperature for 3 hrs. The mixture was then cooled to room temperature and filtered through celite. Ethanol was removed under reduced pressure and the residue was purified by flash-chromatography (SiO$_2$) with n-hexane/acetone/chloroform 6:2:2 as the eluant to give 3.07 g of (1S,3aS,5S,7aR)-1-acetoxymethyl-5-(3-hydroxymethylphenyl)-7a-methylperhydroinden-3a-ol as a white foam.

$^1$H-NMR (300 MHz, CDCl$_3$, ppm from TMS): 1.05 (3H, s); 1.38–2.12 (13H, m); 2.30 (1H, m); 2.70 (1H, m); 4.12 (1H, dd); 4.25 (1H, dd); 4.68 (2H, d); 7.12–7.35 (4H, m).

Starting from 3.05 g of (1S,3aS,5S,7aR)-1-acetoxymethyl-5-(3-hydroxymethylphenyl)-7a-methylperhydroinden-3a-ol, by reaction with tert-butyldimethylchlorosilane using the procedure described by Kendall P. M. et al., (*J. Org. Chem.* 1979, 44, 1421), 3.88 g of (1S,3aS,5S,7aR)-1-acetoxymethyl-5-(3-tert-butyldimethylsilyloxymethylphenyl)-7a-methylperhydroinden-3a-ol were obtained as a white foam. The crude product was dissolved in 30 ml of methanol and 9 ml of 4N NaOH were added. After stirring at room temperature for 8 hrs, the reaction mixture was neutralised with 3N HCl, concentrated in vacuo and extracted with ethyl acetate. The organic layer was dried over sodium sulfate and evaporated to dryness under reduced pressure to give 3.17 g of (1S,3aS,5S,7aR)-1-hydroxymethyl-5-(3-tert-butyldimethylsilyloxymethylphenyl)-7a-methylperhydroinden-3a-ol as a white solid.

$^1$H-NMR (300 MHz, CDCl$_3$, ppm from TMS): 0.09 (6H, s); 1.00 (9H, s); 1.12 (3H, s); 1.38–2.10 (10H, m); 2.30 (1H, m); 2.70 (1H, m); 3.55 (1H, dd); 3.82 (1H, dd); 4.70 (2H, s); 7.12–7.35 (4H, m).

To a solution of 3.25 g of o-iodoxybenzoic acid in 25 ml of DMSO 3.15 g of (1S,3aS,5S,7aR)-1-hydroxymethyl-5-(3-tert-butyldimethylsilyloxymethylphenyl)-7a-methylperhydroinden-3a-ol were added and the resulting solution was stirred for 1.5 hrs. The mixture was then diluted with 10 ml of water and filtered. The residue was extracted with ethyl acetate. The organic layer was washed with water, dried over sodium sulfate and evaporated under reduced pressure. The crude product was dissolved in 10 ml of dioxane and the solution was made acid to pH 1 with 3N HCl and stirred for 1 hr. Then 5% aqueous NaHCO$_3$ was added to reach pH 5 and the reaction mixture was extracted with ethyl acetate. The organic layer was dried over sodium sulfate and evaporated under reduced pressure. The residue was triturated with diethyl ether to give 2.02 g of of the title compound (II-aa) as a white foam.

¹H-NMR (300 MHz, CDCl₃, ppm from TMS): 1.15 (3H, s); 1.50–2.50 (11H, m): 2.72 (1H, m); 4.71 (2H, s); 7.10–7.30 (4H, m); 9.75 (1H, d)

Using the same procedure described above, starting from (1S,3aS,7aR)-1-hydroxymethyl-3a-hydroxy-7a-methyl-5-perhydroindenone and the appropriate aryllithium derivatives the following aldehydes were obtained by successive reactions with acetic anhydride, Raney-nickel, NaOH, o-iodoxybenzoic acid and HCl (in some cases the protection-deprotection reaction of functional groups were not necessary):

(1S,3aS,5S,7aR)-1-Formyl-5-(4-hydroxymethylphenyl)-7a-methylperhydroinden-3a-ol (II-ab)

¹H-NMR (300 MHz, CDCl₃, ppm from TMS): 1.15 (3H, s); 1.40–1.80 (8H, m); 2.00 (1H, m); 2.20 (1H, m); 2.43 (1H, m); 2.72 (1H, m); 4.71 (2H, s); 7.19 (2H, d); 7.25 (2H, d); 9.76 (1H, d).

(1S,3aS,5S,7aR)-1-Formyl-5-(4-hydroxymethylphenyl)-7a-methylperhydroinden-3a-ol (II-ac)

¹H-NMR (300 MHz, CDCl₃, ppm from TMS): 1.15 (3H, s); 1.40–2.55 (11H, m); 2.65 (1H, m); 4.55 (1H, bs); 6.78 (2H, d); 7.08 (2H d); 9.75 (1H, d).

(1S,3aS,5S,7aR)-1-Formyl-5-(3-hydroxymethylphenyl)-7a-methylperhydroinden-3a-ol (II-ab)

¹H-NMR (300 MHz, CDCl₃, ppm from TMS): 1.12 (3H, s); 1.48–2.50 (11H, m); 2.68 (1H, m); 6.68–7.15 (4H m); 9.75 (1H, d).

(1S,3aS,5S,7aR)-1-Formyl-5-(4-hydroxymethylphenyl)-7a-methylperhydroinden-3a-ol (II-ab)

During the synthesis of (II-ab) from the reaction with Raney-nickel, after purification on silica gel and reaction with NaOH, 2.73 g of (1S,3aS,5S,7aR)-1-hydroxymethyl-5-(4-methylphenyl)-7a-methylperhydroinden-3a-ol were obtained as a white foam.

¹H-NMR (300 MHz, CDCl₃, ppm from TMS): 1.15 (3H, s); 1.40–2.25 (10H, m); 2.28 (3H, s); 2.43 (1H, m); 2.70 (1H, m); 3.53 (2H, dd); 3.83 (2H, dd); 7.12 (4H, s).

The title compound (II-ae) was obtained as a dense colourless off by reaction with o-iodoxybenzoic acid, according to the procedure described in Prepn. 1.

¹H-NMR (300 MHz, CDCl₃, ppm from TMS): 1.15 (3H, s); 1.45–2.10 (9H, m); 2.21 (1H, m); 2.32 (3H, s); 2.43 (1H, m); 2.70 (1H, m); 7.12 (4H, s); 9.75 (1H, d).

(1S,3aS,5S,7aR)-1-Formyl-5-(3-methylphenyl)-7a-methylperhydroinden-3a-ol (II-af)

During the synthesis of (II-aa) from the reaction with Raney-nickel, after purification on silica gel and reaction with NaOH, 2.90 g of (1S,3aS,5S,7aR)-1-hydroxymethyl-5-(3-methylphenyl)-7a-methylperhydroinden-3a-ol were obtained as a dense colourless off.

¹H-NMR (300 MHz, CDCl₃, ppm from TMS): 1.08 (3H, s); 1.40–2.10 (10H, m); 2.30 (1H, m); 2.32 (3H, s); 2.68 (1H, m); 3.52 (1H, dd); 3.81 (1H, dd); 7.00–7.35 (4H, m).

The title compound (II-af) (2.00 g) was obtained as a dense colourless oil by reaction with o-iodoxybenzoic acid, according to the procedure described in Prepn. 1.

¹H-NMR (300 MHz, CDCl₃, ppm from TMS): 1.15 (3H, s); 1.48–2.30 (9H, m): 2.33 (3H, s); 2.43 (2H, m); 2.70 (1H, m); 7.00–7.35 (4H, m); 9.78 (1H, d).

(1S,3aS,5S,7aR)-1-Formyl-5-phenyl-7a-methylperhydroinden-3a-ol (II-ab)

¹H-NMR (300 MHz, CDCl₃, ppm from TMS): 1.15 (3H, s); 1.45–2.50 (11H, m); 2.75 (1H, m); 7.18–7.38 (5H, m); 9.73 (1H, d).

(1S,3aS,5S,7aR)-1-Formyl-5-(3-pyridyl)-7a-methylperhydroinden-3a-ol (II-ab)

¹H-NMR (300 MHz, CDCl₃, ppm from TMS): 1.10 (3H, s); 1.40–2.35 (11H, m); 2.75 (1H, m); 7.25 (1H, m); 7.60 (1H, m); 8.40–8.55 (2H, m); 9.73 (1H, d).

(1S,3aS,5S,7aR)-1-Formyl-5-(4-pyridyl)-7a-methylperhydroinden-3a-ol (II-ai)

¹H-NMR (300 MHz, CDCl₃, ppm from TMS): 1.13 (3H, s); 1.25–2.50 (11H, m); 2.65 (1H, m); 7.15 (2H, d); 8.35 (2H, d); 9.73 (1H, d).

PREPARATION 2

(1S,3aS,5S,7aR)-1-Formyl-5[4-(2-dimethylaminoethoxy)phenyl-7a-methylperhydroinden-3a-ol (II-aj)

A mixture of 5.50 g of (1S,3aS,5S,7aR)-1-acetoxymethyl-5-(4-hydroxyphenyl)-7a-methylperhydroinden-3a-ol, obtained as an intermediate in the synthesis of (II-ac), and 1.91 g of sodium hydride (60% dispersion in mineral off) in 10 ml of anhydrous THF was stirred at 0° C. for 15 minutes. A solution of 5.13 g of N,N-dimethyl-2-chloroethylamine in 10 ml of anhydrous THF was added. After stirring at room temperature for 24 hrs, the mixture was diluted with water and extracted with ethyl acetate. The organic layer was dried over sodium sulfate and evaporated to dryness under reduced pressure. The residue was successively reacted with NaOH and o-iodoxybenzoic acid using the same procedure described in Prepn. 1 to give the title compound (II-aj) (1.79 g) as a pale yellow solid.

¹H-NMR (300 MHz, CDCl₃, ppm from TMS): 1.12 (3H, s); 1.45–2.30 (10H, m); 2.43 (6H, s and 1H, m); 2.67 (1H, m); 2.89 (2H, m); 4.10 (2H, m); 6.82 (2H, d); 7.12 (2H d); 9.71 (1H, d).

Using the same procedure described in Prepn. 2, the following aldehyde was obtained:

(1S,3aS,5S,7aR)-1-Formyl-5[3-(2-dimethylaminoethoxy)phenyl-7a-methylperhydroinden-3a-ol (II-ak)

¹H-NMR (300 MHz, CDCl₃, ppm from TMS): 1.12 (3H, s); 1.40–2.31 (10H, m); 2.33 (2H, m); 2.44 (6H, s and 1H, m); 2.65 (1H, m); 4.02 (1H, m); 6.65–7.15 (4H, m); 9.72 (1H, d).

PREPARATION 3

(1S,3aS,5S,7aR)-1-Formyl-5[(Z)-3-hydroxypropyliden]-7a-methylperhydroinden-3a-ol (II-al)

A solution of 20 g of (1S,3aS,7aR)-1-hydroxymethyl-5-spiro-2'-(1',3'-dioxolane)-7a-methylperhydroinden-3a-ol (see Prepn. 1), 9.25 ml of acetic anhydride in 120 ml of anhydrous pyridine was stirred at room temperature for 8 hrs. The mixture was then cooled to 0° C., diluted with 4N HCl to pH 2.5 and extracted with ethyl acetate. The organic layer was washed with 0.1N HCl, dried over sodium sulphate and evaporated to dryness under reduced pressure. The residue was dissolved in 200 ml of 1N PTSA in acetonitrile/water 85:15 and the mixture was kept at room temperature for 8 hrs. Then it was made alkaline with 5% aqueous NaHCO₃, concentrated under reduced pressure and extracted with ethyl acetate. The organic layer was dried over sodium sulfate and evaporated to dryness under reduced pressure to give 13.3 g of (1S,3aS,7aR)-1-acetoxymethyl-3a-hydroxy-7a-methyl-5-perhydroindenone as a white foam.

¹H-NMR (300 MHz, CDCl₃, ppm from TMS): 1.24 (3H, s); 1.55–2.65 (14H, m); 4.05 (1H, dd); 4.20 (1H, dd).

To a suspension of 26.0 g of [2-(1,3-dioxolan-2-yl)ethyl]-triphenylphosphonium bromide in 300 ml of anhydrous THF, cooled at –25° C., 36 ml of 1.6N n-butyllithium in n-hexane were added, under a nitrogen atmosphere. After stirring for 1 hr, a solution of 5.0 g of (1S,3aS,7aR)-1-acetoxymethyl-3a-hydroxy-7a-methyl-5-perhydroindenone in 50 ml of anhydrous THF was added and the resulting mixture was stirred at −20° C. for 4 hrs, then at room temperature per 3 hrs. The reaction mixture was diluted with water and extracted with ethyl acetate. The organic layer was dried over sodium sulfate and evaporated to dryness under reduced pressure. The residue was purified by flash-chromatography (SiO$_2$) with methylene chloride/acetone 95:5 as the eluant to give 1.88 g of (1S,3aS,7aR)-1-acetoxymethyl-5-[(Z)-2-(1,3-dioxolan-2-yl)ethyliden]-7a-methyl-perhydroinden-3a-ol and 1.46 g of (1S,3aS,7aR)-1-acetoxymethyl-5-[(E)-2-(1,3-dioxolan-2-yl)ethyliden]-7a-methylperhydroinden-3a-ol as pale yellow oils.

(Z) isomer: $^1$H-NMR (300 MHz, CDCl$_3$, ppm from TMS): 1.13 (3H, s); 1.40–2.50 (16H, m); 3.88 (4H, m); 4.05 (1H, dd); 4.20 (1H, dd); 4.81 (1H, m), 5.21 (1H, m).

(E) isomer: $^1$H-NMR (300 MHz, CDCl$_3$, ppm from TMS): 1.12 (3H, s); 1.40–2.50 (16H, m); 3.75–4.05 (5H, m); 4.20 (1H, dd); 4.85 (1H, m); 5.36 (1H, m).

A solution of 1.80 g of (1S,3aS,7aR)-1-acetoxymethyl-5-((Z)-2-(1,3-dioxolan-2-yl)ethyliden]-7a-methylperhydroinden-3a-ol in 20 ml of 1N PTSA in acetonitrile/water 85:15 was kept at room temperature for 8 hrs. The mixture was then neutralised with 5% aqueous NaHCO$_3$, concentrated under reduced pressure and extracted with ethyl acetate. The organic layer was dried over sodium sulfate and evaporated to dryness under reduced pressure to give 1.13 g of (1S,3aS,7aR)-1-acetoxymethyl-5-[(Z)-3-hydroxypropyliden]-7a-methylperhydroinden-3a-ol as a dense colourless off.

$^1$H-NMR (300 MHz, CDCl$_3$, ppm from TMS): 1.13 (3H, s); 1.40–2.50 (16H, m); 3.55–3.80 (2H, m); 4.05 (1H, dd); 4.20 (1H, dd); 5.31 (1H, m).

The title compound (II-al) (0.51 g) was obtained as a colourless oil starting from 1.13 g of (1S,3aS,7aR)-1-acetoxymethyl-5-[(Z)-3-hydroxy-1-propyliden]-7a-methylperhydroinden-3a-ol by successive reactions with tert-butyldimethylchlorosilane, NaOH, o-iodoxybenzoic acid and HCl according to the procedure described in Prepn. 1.

$^1$H-NMR (300 MHz, CDCl$_3$, ppm from TMS): 1.03 (3H, s); 1.40–2.50 (12H, m); 2.73 (1H, m); 3.55–3.80 (2H, m); 5.32 (1H, m); 9.73 (1H, d).

(1S,3aS,7aR)-1-Formyl-5-[(E)-3-hydroxypropyliden]-7a-methylperhydroinden-3a-ol (II-am)

The title compound (II-am) was obtained starting from (1S,3aS,7aR)-1-acetoxymethyl-5-[(E)-2-(1,3-dioxolan-2-yl)ethyliden]-7a-methylperhydroinden-3a-ol, obtained during the synthesis of (II-al), by successive reactions with PTSA, NaBH$_4$, tert-butyldimethylchlorosilane, NaOH, o-iodoxybenzoic acid and HCl according to the procedure described in Prepn. 1 and Prepn. 3.

$^1$H-NMR (300 MHz, CDCl$_3$, ppm from TMS): 1.09 (3H, s); 1.45–2.35 (12H, m); 2.60 (1H, m); 3.65 (2H, t); 5.20 (1H, m); 9.72 (1H, d).

Starting from (1S,3aS,7aR)-1-acetoxymethyl-3a-hydroxy-7a-methyl-5-perhydroindenone and the appropriate phosphonium salts and using the procedures described in Prepn. 1 and Prepn. 3, the following aldehydes were obtained:

(1S,3aS,7aR)-1-Formyl-5-[(Z)-3-dimethylaminopropyliden]-7a-methylperhydroinden-3a-ol (II-an)

$^1$H-NMR (300 MHz, CDCl$_3$, ppm from TMS): 1.03 (3H, s); 1.40–2.50 (20H, m); 2.73 (1H, m); 5.22 (1H, m); 9.73 (1H, d)

(1S,3aS,7aR)-1-Formyl-5-[(E)-3-dimethylaminopropyliden]-7a-methylperhydroinden-3a-ol (II-ao)

$^1$H-NMR (300 MHz, CDCl$_3$, ppm from TMS): 0.98 (3H, s); 1.40–2.46 (20H, m); 2.60 (1H, m); 5.20 (1H, m); 9.75 (1H, d).

(1S,3aS,7aR)-1-Formyl-5-[(Z)-benzyliden]-7-a-methylperhydroinden-3a-ol (II-ap)

$^1$H-NMR (300 MHz, CDCl$_3$, ppm from TMS): 1.13 (3H, s); 1.50–2.55 (10H, m); 2.61 (1H, s); 2.82 (1H, d); 6.41 (1H, m); 7.18–7.38 (5H, m); 9.75 (1H, d).

(1S,3aS,7aR)-1-Formyl-5-[(Z)-benzyliden-7-a-methylperhydroinden-3a-ol (II-aq)

$^1$H-NMR (300 MHz, CDCl$_3$, ppm from TMS): 1.09 (3H, s); 1.40–2.60 (11H, m); 6.38 (1H, m); 7.18–7.38 (5H, m); 9.71 (1H, d).

PREPARATION 4

(1S,3aS,7aR)-1-Formyl-5-[(Z)-3-(2-dimethylaminoethoxy-1-propyliden]-7-a-methylperhydroinden-3a-ol (II-ar)

The title compound (II-ar) was obtained starting from (1S,3aS,7aR)-1-acetoxymethyl-5-[(Z)-3-hydroxypropyliden]-7a-methylperhydroinden-3a-ol, intermediate in the synthesis of (II-al), by successive reactions with N,N-dimethyl-2-chloroethylamine and NaH, using the procedure described in Prepn. 2, then NaOH and o-iodoxybenzoic acid, using the same procedures described in Prepn. 1.

$^1$H-NMR (300 MHz, CDCl$_3$, ppm from TMS): 1.03 (3H, s); 1.40–2.50 (20H, m); 2.73 (1H, m); 3.50–3.76 (2H, m); 4.05 (2H, m); 5.32 (1H, m); 9.73 (1H, d).

PREPARATION 5

(1S,3aS,5R,7aR)-1-Formyl-5-(3-hydroxypropyl)-7a-methylperhydroinden-3a-ol (II-as).

A mixture of 5.00 g of (1S,3aS,7aR)-1-acetoxymethyl-5-[(EZ)-2-(1,3-dioxolan-2-yl)ethyliden]-7a-methylperhydroinden-3a-ol, obtained as described in Prepn. 3, without chromatographic purification, 0.05 g of PtO$_2$.2H$_2$O in 5 ml of ethyl acetate was hydrogenated at room temperature and atmospheric pressure for 1 hr. The mixture was filtered through celite, and the solvent was evaporated in vacuo. The residue was purified by flash-chromatography (SiO$_2$) with n-hexane/chloroform/acetone 6:2:2 as the eluant to give 2.10 g of (1S,3aS,5R,7aR)-1-acetoxymethyl-5-[2-(1,3-dioxolan-2-yl)ethyl]-7a-methylperhydroinden-3a-ol as a colourless oil.

$^1$H-NMR (300 MHz, CDCl$_3$, ppm from TMS): 1.12 (3H, s); 1.15–2.30 (19H, m); 3.80–4.03 (4H, m); 4.06 (1H, dd); 4.21 (1H, dd); 4.83 (1H, m).

The title compound (II-as) (0.56 g) was obtained as a dense colourless off starting from 2.00 g of (1S,3aS,5R,7aR)-1-acetoxymethyl-5-[2-(1,3-dioxolan-2-yl)ethyl]-7a-methylperhydroinden-3a-ol, by successive reactions with PTSA, NaBH$_4$, tert-butyldimethylchlorosilane, NaOH, o-iodoxybenzoic acid and HCl using the same procedure described in Prepn. 3.

$^1$H-NMR (300 MHz, CDCl$_3$, ppm from TMS): 1.12 (3H, s); 1.15–2.50 (16H, m); 3.63 (2H, t); 9.72 (1H, d).

Using the chemical transformation described in Prepn. 1, Prepn. 3 and Prepn. 5 and the appropriate intermediates the following aldehydes were obtained:

(1S,3aS,5R,7aR)-1-Formyl-5-(3-dimethylaminopropyl)-7a-methylperhydroinden-3a-ol (II-at)

¹H-NMR (300 MHz, CDCl₃, ppm from TMS): 1.13 (3H, s); 1.40–2.50 (24H, m); 9.70 (1H, d).

(1S,3aS,5R,7aR)-1-Formyl-5-benzyl-7a-methylperhydroinden-3a-ol (II-au)

¹H-NMR (300 MHz, CDCl₃, ppm from TMS): 1.05 (3H, s); 1.06–2.60 (14H, m); 7.10–7.30 (5H, m); 9.70 (1H, d)

(1S,3aS,5R,7aR)-1-Formyl-5-(4-hydroxybenzyl)-7a-methylperhydroinden-3a-ol (II-av)

¹H-NMR (300 MHz, CDCl₃, ppm from TMS): 1.05 (3H, s); 1.06–2.60 (14H, m); 4.55 (1H, bs); 6.78 (2H, d); 7.08 (2H, d); 9.70 (1H, d).

(1S,3aS,5R,7aR)-1-Formyl-5-(4-hydroxymethylbenzyl) 7a-methylperhydroinden-3a-ol (II-aw)

¹H-NMR (300 MHz, CDCl₃, ppm from TMS): 1.05 (3H, s); 1.06–2.60 (14H, m); 4.71 (2H, s); 7.19 (2H, d); 7.25 (2H, d); 9.76 (1H, d).

PREPARATION 6

(1S,3aS,5R,7aR)-1-Formyl-5-cyclohexyl-7a-methylperhydroinden-3a-ol (II-ax)

A mixture of 2.00 g of (1S,3aS,5S,7aR)-1-hydroxymethyl-5-phenyl-7a-methylperhydroinden-3a-ol, intermediate in the synthesis of (II-ag) and 0.85 g of 5% Rhodium on alumina powder in 30 ml of methanol was hydrogenated at room temperature at 60 psi. in a Parr apparatus, for 4 hrs. The mixture was then filtered through celite and the solvent was evaporated under reduced pressure to give 1.94 g of (1S,3aS,5S,7aR)-1-hydroxymethyl-5-cyclohexyl-7a-methylperhydroinden-3a-ol as a white solid.

¹H-NMR (300 MHz, CDCl₃, ppm from TMS): 1.00 (3H, s); 1.05–2.23 (23H, m); 3.50 (1H, dd); 3.79 (1H, dd).

The title compound (II-ax) (1.79 g) was obtained as a white solid starting from 1.90 g of (1S,3aS,5S,7aR)-1-hydroxymethyl-5-cyclohexyl-7a-methylperhydroinden-3a-ol by reaction with o-iodoxybenzoic acid, using the same procedures described in Prepn. 1.

¹H-NMR (300 MHz, CDCl₃, ppm from TMS): 1.00 (3H, s); 1.05–2.42 (23H, m); 9.73 (1H, d).

Using the same procedure described in Prepn. 6 and the appropriate intermediates the following aldehydes were obtained:

(1S,3aS,5R,7aR)-1-Formyl-5-cyclohexylmethyl-7a-methylperhydroinden-3a-ol (II-ay)

¹H-NMR (300 MHz, CDCl₃, ppm from TMS): 1.00 (3H, s); 0.78–2.42 (25H, m); 9.72 (1H, d).

1S,3aS,5S,7aR)-1-Formyl-5-(4-cis-hydroxy-r-1-cyclohexyl)-7a-methylperhydroinden-3a-ol (II-az)

¹H-NMR (300 MHz, CDCl₃, ppm from TMS): 0.98 (3H, s); 1.00–2.45 (21H, m); 3.89 (1H, m); 9.74 (1H, d).

PREPARATION 7

(1S,3aS,5R,7aR)-1-Formyl-5-(4-trans-hydroxy-r-1-cyclohexyl)-7a-methylperhydroinden-3a-ol (II-ba)

Starting from 2.00 g of (1S,3aS,5S,7aR)-1-hydroxymethyl-5-(4-cis-tert-butyldimethylsilyloxy-r-1-cyclohexyl)-7a-methylperhydroinden-3a-ol, intermediate in the synthesis of (II-az), by successive reactions 1.32 g of (1S,3aS,5S,7aR)-1-acetoxymethyl-5-(4-oxocyclohexyl)-7a-methylperhydroinden-3a-ol were obtained as a white foam.

¹H-NMR (300 MHz, CDCl₃, ppm from TMS): 0.98 (3H, s); 1.00–2.52 (24H, m); 4.08 (1H, dd); 4.22 (1H, dd).

To a solution of 1.30 g of (1S,3aS,5S,7aR)-1-acetoxymethyl-5-(4-oxocyclohexyl)-7a-methylperhydroinden-3a-ol in 20 ml of anhydrous THF, cooled at −78° C., a solution of 2.04 g of lithium aluminium tritert-butoxyhydride in 20 ml of anhydrous THF was added dropwise, and the mixture was stirred for 4 hrs under a nitrogen atmosphere. It was then diluted with 5% aqueous acetic acid, concentrated in vacuo and extracted with ethyl acetate. The organic layer was dried over sodium sulfate and evaporated to dryness under reduced pressure. The title compound (II-ba) (0.48 g) was obtained as a white solid by successive reactions with tert-butyldimethylchlorosilane, NaOH, o-iodoxybenzoic acid and HCl, using the same procedures described in Prepn. 1.

¹H-NMR (300 MHz, CDCl₃, ppm from TMS): 0.98 (3H, s); 1.00–2.45 (21H, m); 3.51 (1H, m); 9.74 (1H, d).

PREPARATION 8

(1R,3aS,5S,7aR)-1-[(E)-2-Formyl-1-ethenyl]-5-(4-hydroxyphenyl)-7a-methylperhydroinden-3a-ol (II-bb)

To a suspension of 0.54 g of NaH (60% dispersion in oil), in 40 ml of anhydrous THF, cooled at 0° C., 1.04 ml of trimethyl phosphonoacetate were added and the mixture was stirred at room temperature for 0.5 hr. After cooling at 0° C., a solution of 3.85 g of (1S,3aS,5S,7aR)-1-formyl-5-(4-tert-butyldimethylsilyloxyphenyl)-7a-methylperhydroinden-3a-ol, intermediate in the synthesis of (II-ac) in 10 ml of anhydrous THF was added and the mixture was stirred at room temperature for 1 hr. It was then diluted with 5% aqueous NaH₂PO₄.H₂O, concentrated under reduced pressure and extracted with ethyl acetate. The organic layer was dried over sodium sulfate and evaporated to dryness under reduced pressure to give 3.95 g of (1R,3aS,5S,7a-1-[(E)-2-methoxycarbonyl-1-ethenyl]-5-(4-tert-butyldimethylsilyloxyphenyl)-7a-methylperhydroinden-3a-ol as a white solid.

¹H-NMR (300 MHz, CDCl₃, ppm from TMS): 0.20 (6H, s); 0.85 (3H, s); 1.00 (9H, s); 1.40–1.95 (8H, m); 2.00–2.25 (2H, m); 2.35 (1H, m); 2.65 (1H, m); 3.70 (3H, s); 5.62 (1H, d); 6.75 (2H, d); 7.08 (2H, d); 7.15 (1H, dd).

To a solution of 3.90 g of (1R,3aS,5S,7aR)-1-[(E)-2-methoxycarbonyl-1-ethenyl]-5-(4-tert-butyl-dimethylsilyloxyphenyl)-7a-methylperhydroinden-3a-ol in 50 ml of anhydrous THF, cooled at −78° C., 45 ml of 1N DIBAH in THF were added and the mixture was stirred at −78° C. for 1 hr, then at room temperature for 8 hrs. The reaction mixture was cooled to 0° C. and 100 ml of 1N H₂SO₄ were cautiously added and stirring was continued at room temperature for 1 hr. The mixture was then extracted with ethyl acetate. The organic layer was dried over sodium sulfate and evaporated to dryness under reduced pressure. The residue was purified by flash chromatography (SiO₂) with n-hexane/ethyl acetate 7:3 as the eluant to give 2.95 g of (1R,3aS,5S,7aR)-1-[(E)-3-hydroxy-1-propenyl]-5-(4-tert-butyldimethylsilyloxyphenyl)-7a-methylperhydroinden-3a-ol as a white solid.

¹H-NMR (300 MHz, CDCl₃, ppm from TMS): 0.20 (6H, s); 0.85 (3H, s); 1.00 (9H, s); 1.40–2.30 (11H, m); 2.65 (1H, m); 4.10 (2H, dd); 5.45 (1H, dt); 5.87 (1H, dd); 6.75 (2H, d); 7.08 (2H, d).

To a solution of 2.90 g of (1R,3aS,5S,7aR)-1-[(E)-3-hydroxy-1-propenyl]-5-(4-tert-butyldimethyl-silyloxyphenyl)-7a-methylperhydroinden-3a-ol in 40 ml of dioxane, 13.80 g of MnO₂ were added while cooling in an ice bath. The mixture was stirred at room temperature for 1 hr, filtered through celite and the filtrate was made acid to pH 1 with 3N HCl and, using the same procedure described in Prepn. 1, the title compound (II-bb) (2.75 g) was obtained as a white solid.

¹H-NMR (300 MHz, CDCl₃, ppm from TMS): 0.85 (3H, s); 1.40–2.30 (10H, m); 2.50 (1H, m); 2.65 (1H, m); 4.55 (1H, bs); 5.92 (1H, dd); 6.78 (2H, d); 7.08 (2H, d); 7.11 (1H, dd); 9.51 (1H, d).

Using the same procedure described in Prepn. 8, starting from the appropriate 1-formyl-7a-methylperhydroinden-3a- ol derivative and trimethyl phosphonoacetate or triethyl 2-phosphonopropionate, the following aldehydes were obtained:

(1R,3aS,5S,7aR)-1-[(E)-2-Formyl-1-propenyl]-5-(4-hydroxyphenyl)-7a-methylperhydroinden-3a-ol (II-bc)

$^1$H-NMR (300 MHz, CDCl$_3$, ppm from TMS): 0.85 (3H, s); 1.40–2.40 (10H, m); 1.72 (3H, d); 2.65 (1H, m); 2.80 (1H, m); 4.55 (1H, bs); 6.78 (3H, m); 7.08 (2H, d); 9.41 (1H, s).

(1R,3aS,5S,7aR)-1-[(E)-2-Formyl-1-propenyl]-5-(3-hydroxyphenyl)-7a-methylperhydroinden-3a-ol (II-bd)

$^1$H-NMR (300 MHz, CDCl$_3$, ppm from TMS): 0.85 (3H, s); 1.40–2.50 (10H, m); 1.72 (3H, d); 2.68 (1H, m); 2.80 (1H, m); 6.68–7.15 (4H, m); 9.41 (1H, s).

The following aldehydes were obtained directly from the corresponding 1-formyl-7a-methylperhydroinden-3a-ol derivatives described in Prepn. 1, using the same procedure described in Prepn. 8, without the hydrolysis with HCl:

(1R,3aS,5S,7aR)-1-[(E)-2-Formyl-1-ethenyl-]-5-phenyl-7a-methyl-perhydroinden-3a-ol (II-be)

$^1$H-NMR (300 MHz, CDCl$_3$, ppm from TMS): 0.85 (3H, s); 1.45–2.30 (10H, m); 2.50 (1H, m); 2.75 (1H, m); 5.93 (1H, dd); 7.11 (1H, dd); 7.18–7.38 (5H, m); 9.51 (1H, d).

(1R,3aS,5S,7aR)-1-[(E)-2-Formyl-1-ethenyl-]-5-cyclohexyl-7a-methylperhydroinden-3a-ol (II-bf)

$^1$H-NMR (300 MHz, CDCl$_3$, ppm from TMS): 0.88 (3H, s); 0.90–1.89 (20H, m); 2.07–2.30 (2H, m); 2.50 (1H, m); 5.92 (1H, dd); 7.10 (1H, dd); 9.50 (1H, d).

(1R,3aS,5S,7aR)-1-[(E)-2-Formyl-1-propenyl-]-5-phenyl-7a-methylperhydroinden-3a-ol (II-bg) $^1$H-NMR (300 MHz, CDCl$_3$, ppm from TMS): 0.85 (3H, s); 1.45–2.40 (10H, m); 1.72 (3H, d); 2.70 (2H, m); 6.79 (1H, dd); 7.18–7.38 (5H, m); 9.42 (1H, s).

(1R,3aS,5S,7aR)-1-[(E)-2-Formyl-1-propenyl-]-5-cyclohexyl-7a-methylperhydroinden-3a-ol (II-bh)

$^1$H-NMR (300 MHz, CDCl$_3$, ppm from TMS): 0.85 (3H, s); 0.90–1.65 (20H, m); 1.73 (3H, d); 2.05–2.40 (2H, m); 2.80 (1H, m); 6.80 (1H, dd); 9.40 (1H, d).

(1R,3aS,5S,7aR)-1-[(E)-2-Formyl-1-propenyl-]-5-(4-methylphenyl)-7a-methylperhydroinden-3a-ol (II-bi)

$^1$H-NMR (300 MHz, CDCl$_3$, ppm from TMS): 0.85 (3H, s); 1.45–2.50 (13H, m); 1.72 (3H, d); 2.70 (1H, m); 2.78 (1H, m); 6.79 (1H, dd); 7.12 (4H, s); 9.42 (1H, s).

(1R,3aS,5S,7aR)-1-[(E)-2-Formyl-1-propenyl-]-5-(3-methylphenyl)-7a-methylperhydroinden-3a-ol (II-bj)

$^1$H-NMR (300 MHz, CDCl$_3$, ppm from TMS): 0.85 (3H, s); 1.45–2.50 (13H, m); 1.72 (3H, d); 2.70 (1H, m); 2.80 (1H, m); 6.80 (1H, dd); 7.00–7.35 (4H, m); 9.41 (1H, s).

PREPARATION 9

(1S,3aS,5S,7aR)-1-Formyl-5-(2-hydroxyethoxy)-7a-methylperhydroinden-3a-ol (II-bk)

To a solution of 5.00 g of (1S,3aS,7aR)-1-acetoxymethyl-3a-hydroxy-7a-methyl-5-perhydroindenone (see Prepn. 3) in 50 ml of methanol cooled at 0° C., 0.77 g of NaBH$_4$ were added and the mixture was stirred for 1 hr. It was then diluted with 10 ml of 5% aqueous NaH$_2$PO$_4$.H$_2$O, concentrated in vacuo and extracted with ethyl acetate. The organic layer was dried over sodium sulfate and evaporated to dryness under reduced pressure. The residue was purified by flash-chromatography (SiO$_2$) with n-hexane/chloroform/acetone 4:3:3 as the eluant to give 2.18 g of (1S,3aS,5S,7aR)-1-acetoxymethyl-7a-methylperhydroinden-3a,5-diol as a white foam.

$^1$H-NMR (300 MHz, CDCl$_3$, ppm from TMS): 1.15 (3H, s); 1.40–2.30 (14H, m); 3.98 (1H, m); 4.05–4.20 (2H, m).

A mixture of 2.15 g of (1S,3aS,5S,7aR)-1-acetoxymethyl-7a-methylperhydroinden-3a,5-diol and 1.45 g of NaH (60% dispersion in oil) in 4 ml of anhydrous THF was stirred at 0° C. for 15 min. A solution of 6.00 g of 2-bromomethyl-1,3-dioxolane in 10 ml of anhydrous THF was added and the mixture was stirred at room temperature for 8 hrs. It was then diluted with 30 ml of 5% aqueous NaH$_2$PO$_4$.H$_2$O, concentrated under reduced pressure and extracted with ethyl acetate. The organic layer was dried over sodium sulfate and evaporated to dryness under reduced pressure.

The title compound (II-bk) (0.52 g) was obtained as a white solid by successive reactions with PTSA, NaBH$_4$, tert-butyldimethylchlorosilane, NaOH, o-iodoxybenzoic acid and HCl using the procedures described in Prepn. 3.

$^1$H-NMR (300 MHz, DMSO-d$_6$, ppm from TMS): 1.10 (3H, s); 1.40–2.30 (10H, m); 2.20 (1H, m); 3.42–3.71 (4H, m); 3.98 (1H, m); 9.54 (1H, d).

The following aldehyde is obtained with the procedure described in Prep. 9, using the alkylation method with NaH and N,N-dimethyl-2-chloroethylamine, described in Prep. 2.

(1S,3aS,5S,7aR)-1-Formyl-5-[2-(2-dimethylaminoethoxy)ethoxy]-7a-methylperhydroinden-3a-ol (II-bl)

$^1$H-NMR (300 MHz, CDCl$_3$, ppm from TMS): 1.00 (3H, s); 1.40–2.30 (10H, m); 2.33 (6H, s); 2.43 (3H, m); 3.42–3.61 (4H, m); 3.89–4.00 (3H, m); 9.74 (1H, d).

PREPARATION 10

(1S,3aS,5S,7aR)-1-Formyl-5-[(E)-4-hydroxy-1-butenyl)]-7a-methylperhydroinden-3a-ol (II-bm)

Starting from 10.0 g of (1S,3aS,7aR)-1-acetoxymethyl-3a-hydroxy-7a-methyl-5-perhydroindenone (see Prepn. 3), by successive reactions with methyltriphenylphosphonium bromide, BH$_3$.SMe$_2$ and NaBO$_3$.4H$_2$O, and o-iodoxybenzoic acid, 3.20 g of (1S,3aS,5S,7aR)-1-acetoxymethyl-3a-hydroxy-5-formyl-7a-methylperhydroindene were obtained as a dense colourless oil, using the same procedures described in Prepn. 1.

$^1$H-NMR (300 MHz, CDCl$_3$, ppm from TMS): 1.00 (3H, s); 1.20–2.20 (14H, m); 2.41 (1H, m); 4.05 (1H, dd); 4.20 (1H, dd); 9.60 (1H, d).

To a suspension of 23.0 g of (3-hydroxypropyl) triphenylphosphonium bromide in 280 ml of anhydrous THF cooled at –25° C., 36.0 ml of 1.6N n-butyllithium in n-hexane were added dropwise under a nitrogen atmosphere and the mixture was stirred at –25° C. for 1 hr. A solution of 3.20 g of (1S,3aS,5S,7aR)-1-acetoxymethyl-3a-hydroxy-5-formyl-7a-methylperhydroindene in 32 ml of anhydrous THF was added and the reaction mixture was kept at –20° C. for 4 hrs, then warmed to room temperature and stirred for 3 hrs. The mixture was diluted with 5% aqueous NaH$_2$PO$_4$.H$_2$O, concentrated under reduced pressure and extracted with ethyl acetate. The organic layer was dried over sodium sulfate and evaporated to dryness under reduced pressure. The residue was purified by flash-chromatography (SiO$_2$) with n-hexane/chloroform/acetone 6:2:2 to give 2.23 g of (1S,3aS,5S,7aR)-1-acetoxymethyl-5-[(E)-4-hydroxy-1-butenyl)-7a-methylperhydro-inden-3a-ol from which, by reaction with tert-butyldimethylchlorosilane, following the procedure, described in Prepn. 1, 2.94 g of (1S,3aS,5S,7aR)-1-acetoxymethyl-5-[(E)-4-tert-butyldimethylsilyl-oxy-1-butenyl)-7a-methylperhydroinden-3a-ol were obtained as a white foam.

$^1$H-NMR (300 MHz, CDCl$_3$, ppm from TMS): 0.09 (6H, s); 1.00 (9H, s); 1.10 (3H, s); 1.37–2.45 (17H, m); 3.65 (2H, m); 4.05 (1H, dd); 4.20 (1H, dd); 5.32 (1H, dd); 5.55 (1H, dd).

The title compound (II-bm) (1.23 g) was obtained as a white foam, starting from 2.90 g of (1S,3aS,5S,7aR)-1-acetoxymethyl-5-[(E)-4-tert-butyldimethylsilyloxy-1- butenyl)-7a-methylperhydroinden-3a-ol by successive reactions with NaOH, o-iodoxybenzoic acid and HCl using the same procedures described in Prepn. 1

¹H-NMR (300 MHz, CDCl₃, ppm from TMS): 1.10 (3H, s); 1.37–2.50 (14H, m); 3.72 (2H, m); 5.32 (1H, dd); 5.55 (1H, dd); 9.73 (1H, d).

Using the same procedure described in Prepn. 10, starting from the appropriate phosphonium salt, after reaction with o-iodoxybenzoic acid, using the same procedures described in Prepn. 1, the following aldehyde was obtained:

(1S,3aS,5S,7aR)-1-Formyl-5-[E -4-dimethylamino-1-butenyl)]-7a-methylperhydroinden-3a-ol (II-bn)

¹H-NMR (300 MHz, CDCl₃, ppm from TMS): 1.10 (3H, s); 1.37–2.55 (22H, m); 5.32 (2H, m); 9.73 (1H, d).

PREPARATION 11

(1S,3aS,5S,7aR)-1-Formyl-5-(4-hydroxybutyl)-7a-methylperhydroinden-3a-ol (II-bo)

The title compound (II-bo) (0.68 g) was obtained as a white foam starting from 0.75 g of (1S,3aS,5S,7aR)-1-formyl-5-[(E)-4-hydroxy-1-butenyl)-7a-methylperhydroinden-3a-ol (II-bm) by hydrogenation with 0.08 g of 5% Pd on activated carbon in 2 ml of ethyl acetate at room temperature and atmospheric pressure for 1 hr according to a general methodology.

¹H-NMR (300 MHz, CDCl₃, ppm from TMS): 1.10 (3H, s); 1.37–2.50 (16H, m); 3.72 (2H, m); 9.73 (1H, d).

Using the same procedure described in Prepn. 11, starting from (II-bn), the following aldehyde was obtained:

1S,3aS,5s,7aR)-1-Formyl-5-(4-dimethylaminobutyl)-7a-methylperhydroinden-3a-ol (II-bp)

¹H-NMR (300 MHz, CDCl₃, ppm from TMS): 1.10 (3H, s); 1.37–2.55 (24H, m); 9.73 (1H, d).

Compounds of general formula (I) prepared according to the invention and their pharmaceutically acceptable salts are useful agents for the treatment of cardiovascular disorders such as heart failure and hypertension.

Moreover said compounds (I) show good affinity for the receptor site of the Na⁺,K⁺-ATPase and good inhibition of the said enzyme.

To test the affinity for the receptor site of the Na⁺,K⁺-ATPase and the agonist or antagonist activity on the enzyme, the following tests were used:

a) displacement of the specific ³H-ouabain binding from the Na⁺,K⁺-ATPase receptor purified according to Jorghensen (Jorghensen P., BBA, 1974, 356, 36) and Erdmann (Erdmann E. et al., Arzneim. Forsh., 1984, 34, 1314);

b) inhibition of the activity of the purified Na⁺,K⁺-ATPase measured as % of hydrolysis of ³²P-ATP in presence and in absence of the tested compound (Doucet A. et al., Am. J. Physiol., 1986, 251, F851)

Systolic blood pressure (SBP) and heart rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5% (w/v), was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment maintained blood pressure low or reestablished the basal values.

The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., Japan J. Pharmacol. 1979, 29, 171; Takeda K. et al. Japan J. Pharmacol., 1982, 32, 283; Richer C. et al. Eur. J. Pharmacol, 1978, 47.393).

The affinity and the inhibitory activity of some compounds in the two tests are shown in the following table:

|  | Binding ³H-Ouab. Displacement -log IC₅₀ | Inhibitory Activity -log IC₅₀ |
| --- | --- | --- |
| Comp. I-ap | 5,7 | 4,4 |
| Comp. I-au | 5,2 | 4,3 |
| Comp. I-ax | 5,8 | 4,4 |
| Comp. I-bb | 5,8 | 4,6 |
| Comp. I-bc | 5,3 | 4,3 |
| Comp. I-bg | 5,4 | 4,5 |
| Comp. I-bh | 5,2 | 4,3 |
| Comp. I-bx | 4,9 | 4,2 |
| Comp. I-by | 4,7 | 4,2 |
| Comp. I-df | 5,2 | 4,3 |
| Comp. I-di | 5,1 | 4,3 |

The activity of some new compound in preventing the development of hypertension is shown in the following table:

| EFFECT OF 5 WEEK-TREATMENT IN SPONTANEOUS HYPERTENSIVE RATS (MHS) ON THE DEVELOPMENT OF HYPERTENSION | | | | |
| --- | --- | --- | --- | --- |
| Compound | Rats | DOSE* mg/Kg/os | SBP mm Hg | HR bEATS/min. |
| Controls | 7 | Methocel | 172 +/- 5,0 | 380 +/- 6,3 |
| Comp. I-ap | 7 | 20 | 155 +/- 4,3 | 370 +/- 10,5 |
| Comp. I-ax | 7 | 20 | 156 +/- 4,6 | 383 +/- 11,4 |
| Comp. I-bc | 7 | 20 | 160 +/- 7,8 | 377 +/- 10,5 |

*in Methocel 0.5% p/v

What is claimed is:

1. A 1,5 disubstituted 5a-methylperhydroinden-3a-ol derivative of formula (I), or a pharmaceutically acceptable salt thereof:

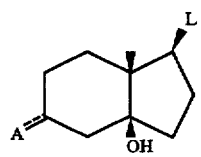 (I)

wherein:
either
the symbol ---- represents a single bond,
the group A is in cis configuration with respect to the 3a-hydroxy, 7a-methyl and 1-L groups, and
A is (CH=CH)ₘ~(CH₂)ₙOR, (CH=CH)ₘ~(CH₂)ₙNR¹R², (CH=CH)ₘ~(CH₂)ₚB, OH, O(CH₂)qOR, O(CH₂)qNR¹R² or O(CH₂)ᵣB;
q is an integer from 2 to 5;
r is an integer from 1 to 2;
or
the symbol ---- represents a double bond,
A is oxygen, CH~(CH=CH)ₛ~(CH₂)ₙOR, CH~(CH=CH)ₛ~(CH₂)ₙNR¹R² or CH~(CH=CH)ₛ~(CH₂)ₚB;

R is hydrogen, unsubstituted C₁–C₄ alkyl or C₁–C₄ alkyl substituted by NR¹R²;

either

R$^1$ and R$^2$, which may be the same or different, are independently hydrogen or C$_1$-C$_4$ alkyl;

B is a five-membered unsaturated or six-membered unsaturated or saturated monocarbocyclic ring and the monocarbocycle may be unsubstituted or substituted by one or more substituents selected from the group consisting of C$_1$-C$_4$ alkyl, halogen, (CH$_2$)$_m$OR, and (CH$_2$)$_m$NR$^1$R$^2$;

n is an integer from 1 to 6;

p is an integer from 0 to 2;

m is an integer from 0 to 2;

L is [CH=C(R$^3$)]$_s$CH=NR$^4$ or [CH=C(R$^3$)]$_s$CH$_2$NHR$^4$, in the E configuration;

s is 0 or 1;

R$^3$ is hydrogen or CH$_3$;

R$^4$ is NHC(=N~R$^5$)NR$^6$R$^7$ or OR$^8$;

the symbol ~ represents a Z or E configuration;

R$^5$ is hydrogen or C$_1$-C$_4$ alkyl, R$^6$ and R$^7$, which may be the same or different, are independently hydrogen, unsubstituted C$_1$-C$_4$ alkyl or C$_1$-C$_4$ substituted by NR$^9$R$^{10}$;

R$^8$ is hydrogen, CH$_3$, unsubstituted C$_2$-C$_6$ alkyl, C$_2$-C$_6$ alkyl substituted with NR$^9$R$^{10}$ or NHC(=NH)NH$_2$; and R$^9$ and R$^{10}$, which may be the same or different, are independently hydrogen or C$_1$-C$_4$ alkyl.

2. The compound of claim 1, wherein the symbol ---- represents a single bond.

3. The compound of claim 1, wherein the symbol ---- represents a double bond.

4. The compound of claim 1, wherein R is selected from the group consisting of hydrogen, methyl, ethyl, n-propyl, n-butyl, 2-aminoethyl, 3-aminopropyl, 2-dimethylaminoethyl, 3-dimethylaminopropyl.

5. A compound according to claim 1, which is selected from:

(1S,3aS,5S,7aR)-1-[(E)-guanidinoimino]methyl-5-phenyl-7a-methylperhydroinden-3a-ol (1S,3aS,5S,7aR)-1-[(E)-hydroxyimino]methyl-5-phenyl-7a-methylperhydroinden-3a-ol (1S,3aS,5S,7aR)-1-[(E)-2-aminoethoxyimino]methyl-5-phenyl-7a-methylperhydroinden-3a-ol (1S,3aS,5S,7aR)-1-[(E)-3-aminopropoxyimino]methyl-5-phenyl-7a-methylperhydroinden-3a-ol (1S,3aS,5S,7aR)-1-[(E)-4-aminobutoxyimino]methyl-5-phenyl-7a-methylperhydroinden-3a-ol (1S,3aS,5S,7aR)-1-[(E)-2-dimethylaminoethoxyimino]methyl-5-phenyl-7a-methylperhydroinden-3a-ol (1S,3aS,5S,7aR)-1-[(E)-3-dimethylaminopropoxyimino]methyl-5-phenyl-7a-methylperhydroinden-3a-ol (1S,3aS,5S,7aR)-1-[(E)-4-dimethylaminobutoxyimino]methyl-5-phenyl-7a-methylperhydroinden-3a-ol (1S,3aS,5S,7aR)-1-[(E)-2-guanidinoethoxyimino]methyl-5-phenyl-7a-methylperhydroinden-3a-ol (1S,3aS,5S,7aR)-1-guanidinoaminomethyl-5-phenyl-7a-methylperhydroinden-3a-ol (1S,3aS,5S,7aR)-1-(2-aminoethoxyamino)methyl-5-phenyl-7a-methylperhydroinden-3a-ol (1S,3aS,5S,7aR)-1-(3-aminopropoxyamino)methyl-5-phenyl-7a-methylperhydroinden-3a-ol (1S,3aS,5S,7aR)-1-(2-dimethylaminoethoxyamino)methyl-5-phenyl-7a-methylperhydroinden-3a-ol (1S,3aS,5S,7aR)-1-(3-dimethylaminopropoxyamino)methyl-5-phenyl-7a-methylperhydroinden-3a-ol (1R,3aS,5S,7aR)-1-[(E,E)-3-guanidinoimino-1-propenyl]-5-phenyl-7a-methylperhydroinden-3a-ol (1R,3aS,5S,7aR)-1-[(E,E)-3-(2-aminoethoxyimino)-1-propenyl]-5-phenyl-7a-methylperhydroinden-3a-ol (1R,3aS,5S,7aR)-1-[(E,E)-3-(2-dimethylaminoethoxyimino)-1-propenyl]-5-phenyl-7a-methylperhydroinden-3a-ol (1R,3aS,5S,7aR)-1-[(E)-3-guanidinoamino-1-propenyl]-5-phenyl-7a-methylperhydroinden-3a-ol (1R,3aS,5S,7aR)-1-[(E)(-3-(2-aminoethoxyamino])-1-propenyl]-5-phenyl-7a-methylperhydroinden-3a-ol (1R,3aS,5S,7aR)-1-[(E)-3-(2-dimethylaminoethoxyamino)-1-propenyl]-5-phenyl-7a-methylperhydroinden-3a-ol (1R,3aS,5S,7aR)-1-[(E,E)-2-methyl-3-guanidinoimino-1-propenyl]-5-phenyl-7a-methylperhydroinden-3a-ol (1R,3aS,5S,7aR)-1-[(E,E)-2-methyl-3-(2-aminoethoxyimino])-1-propenyl]-5-phenyl-7a-methylperhydroinden-3a-ol (1R,3aS,5S,7aR)-1-[(E,E)-2-methyl-3-(2-dimethylaminoethoxyimino)-1-propenyl]-5-phenyl-7a-methylperhydroinden-3a-ol (1R,3aS,5S,7aR)-1-[(E)-2-methyl-3-guanidinoamino-1-propenyl]-5-phenyl-7a-methylperhydroinden-3a-ol (1R,3aS,5S,7aR)-1-[(E)-2-methyl-3-(2-aminoethoxyamino])-1-propenyl]-5-phenyl-7a-methylperhydroinden-3a-ol (1R,3aS,5S,7aR)-1-[(E)-2-methyl-3-(2-dimethylaminoethoxyamino)-1-propenyl]-5-phenyl-7a-methylperhydroinden-3a-ol.

6. The compound of claim 1, wherein B is selected from the group consisting of phenyl, cyclopentyl and cyclohexyl.

7. The compound of claim 1, wherein the NR$^6$R$^7$ group is selected from the group consisting of amino, methylamino, dimethylamino, pyrrolidinyl, piperidinyl, 2-dimethylaminoetil and 2-diethylaminoetil.

8. A composition, comprising:

(a) a pharmaceutically acceptable carrier and/or diluent; and (b) a 1,5 disubstituted 5a-methylperhydroinden-3a-ol derivative of formula (I), or a pharmaceutically acceptable salt thereof:

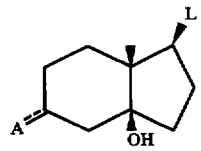

(I)

wherein:

either the symbol ---- represents a single bond, the group A is in cis configuration with respect to the 3a-hydroxy, 7a-methyl and 1-L groups, and A is (CH=CH)$_m$~(CH$_2$)$_n$OR, (CH=CH)$_m$~(CH$_2$)$_n$NR$^1$R$^2$, (CH=CH)$_m$~(CH$_2$)$_p$B, OH, O(CH$_2$)$_q$OR, O(CH$_2$)$_q$NR$^1$R$^2$ or O(CH$_2$)$_p$B;

q is an integer from 2 to 5;

r is an integer from 1 to 2;

or the symbol ---- represents a double bond,

A is oxygen, CH~(CH=CH)$_s$~(CH$_2$)$_n$OR, CH~(CH=CH)$_s$~(CH$_2$)$_n$NR$^1$R$^2$ or CH~(CH=CH)$_s$~(CH$_2$)$_p$B;

R is hydrogen, unsubstituted $C_1$–$C_4$ alkyl or $C_1$–$C_4$ alkyl substituted by $NR^1R^2$;

either

R$^1$ and R$^2$, which may be the same or different, are independently hydrogen or $C_1$–$C_4$ alkyl;

B is a five-membered unsaturated or six-membered unsaturated or saturated monocarbocyclic ring, and the monocarbocycle may be unsubstituted or substituted by one or more substituents selected from the group consisting of $C_1$–$C_4$ alkyl, halogen, $(CH_2)_m OR$, and $(CH_2)_m$, $NR^1R^2$;

n is an integer from 1 to 6;

p is an integer from 0 to 2;

m is an integer from 0 to 2;

L is $[CH=C(R^3)]_s CH=NR^4$ or $[CH=C(R^3)]_s CH_2NHR^4$, in the E configuration;

s is 0 or 1;

$R^3$ is hydrogen or $CH_3$;

$R^4$ is $NHC(=N\sim R^5)NR^6R^7$ or $OR^8$;

the symbol $\sim$ represents a Z or E configuration;

$R^5$ is hydrogen or $C_1$–$C_4$ alkyl, $R^6$ and $R^7$ which may be the same or different, are independently hydrogen, unsubstituted $C_1$–$C_4$ alkyl or $C_1$–$C_4$ substituted by $NR^9R^{10}$; $R^8$ is hydrogen, $CH_3$, unsubstituted $C_2$–$C_6$ alkyl, $C_2$–$C_6$ alkyl substituted with $NR^9R^{10}$ or $NHC(=NH)NH_2$; and $R^9$ and $R^{10}$, which may be the same or different, are independently hydrogen or $C_1$–$C_4$ alkyl.

* * * * *